US011419915B2

(12) United States Patent
Zondag et al.

(10) Patent No.: US 11,419,915 B2
(45) Date of Patent: Aug. 23, 2022

(54) COMPOSITIONS AND METHODS FOR THE TREATMENT OF MALNUTRITION

(71) Applicant: VitalneXt B.V., Amersfoort (NL)

(72) Inventors: Gerben Carolus Martinus Zondag, Amersfoort (NL); Reinder Strijker, Amersfoort (NL)

(73) Assignee: VITALNEXT B.V., Amersfoort (NL)

( * ) Notice: Subject to any disclaimer, the term of this patent is extended or adjusted under 35 U.S.C. 154(b) by 0 days.

(21) Appl. No.: 16/906,541

(22) Filed: Jun. 19, 2020

(65) Prior Publication Data

US 2020/0316170 A1    Oct. 8, 2020

Related U.S. Application Data

(62) Division of application No. 15/738,215, filed as application No. PCT/EP2016/064636 on Jun. 24, 2016, now abandoned.

(30) Foreign Application Priority Data

Jun. 25, 2015 (NL) ..................................... 2015032

(51) Int. Cl.
| | |
|---|---|
| A23L 33/175 | (2016.01) |
| A61K 38/17 | (2006.01) |
| A23L 33/155 | (2016.01) |
| A23L 33/19 | (2016.01) |
| A23L 33/10 | (2016.01) |
| A23L 33/105 | (2016.01) |
| A23P 10/40 | (2016.01) |
| A61P 3/02 | (2006.01) |
| A61K 9/00 | (2006.01) |
| A61K 31/198 | (2006.01) |
| A61K 31/56 | (2006.01) |
| A61K 31/592 | (2006.01) |
| A61K 31/593 | (2006.01) |

(52) U.S. Cl.
CPC .......... *A61K 38/1709* (2013.01); *A23L 33/10* (2016.08); *A23L 33/105* (2016.08); *A23L 33/155* (2016.08); *A23L 33/175* (2016.08); *A23L 33/19* (2016.08); *A23P 10/40* (2016.08); *A61K 9/0095* (2013.01); *A61K 31/198* (2013.01); *A61K 31/56* (2013.01); *A61K 31/592* (2013.01); *A61K 31/593* (2013.01); *A61P 3/02* (2018.01); *A23V 2002/00* (2013.01)

(58) Field of Classification Search
None
See application file for complete search history.

(56) References Cited

U.S. PATENT DOCUMENTS

| 8,021,701 | B1 | 9/2011 | Perry |
| 2003/0229029 | A1 | 12/2003 | Laudadio |
| 2011/0250317 | A1 | 10/2011 | Secretin |
| 2013/0203712 | A1 | 8/2013 | Adams et al. |
| 2014/0044685 | A1 | 2/2014 | Greenberg et al. |
| 2015/0164833 | A1 | 6/2015 | Kuang et al. |

FOREIGN PATENT DOCUMENTS

| CN | 102210837 A | 10/2011 |
| EP | 2705844 | 3/2014 |
| EP | 3313207 B1 | 12/2019 |
| WO | 2009143097 A1 | 11/2009 |
| WO | 2012005568 A1 | 7/2010 |
| WO | 2012143403 A1 | 4/2011 |
| WO | 2012143405 A1 | 4/2011 |
| WO | 2011146768 A1 | 11/2011 |
| WO | 2012005582 A1 | 1/2012 |
| WO | WO 2012/005568 | 1/2012 |
| WO | 2012143402 A1 | 10/2012 |
| WO | 2012143404 A1 | 10/2012 |
| WO | WO 2012/170546 | 12/2012 |
| WO | WO 2013/150468 | 10/2013 |
| WO | WO 2014/055905 | 4/2014 |
| WO | WO 2014/099904 | 6/2014 |
| WO | WO 2015/094533 | 6/2015 |

OTHER PUBLICATIONS

Lobo, et al., Ursolic acid has no additional effect on muscle strength and mass in active men undergoing a high-protein diet and resistance training: A double-blind and placebo-controlled trial, Clinical Nutrition 40 (2021) 581-589. (Year: 2021).*
Sun et al, British Journal of Nutrition (2016), 116, 1216-1221.
Kunkel, S.D., et al., Ursolic Acid Increases Skeletal Muscle and Brown Fat and Decreases Diet-Induced Obesity, Glucose Intolerance and Fatty Liver Disease. PLoS ONE 7(6): e39332. Doi10.1371/journal.pone.0039332 (Year: 2012).
Kunkel, S.D. et al., Cell Metabolism 13, 627-638, 2011.
Schmid and Walther (Natural Vitamin D Content in Animal Products, Adv. Nutr. 2013, 4(4): 453-462.
Butler, et al., Fat Composition of Organic and Conventional Retail Milk in Northeast England, J. Dairy Sci. 94: 24-36, 2011 (2011).
Freijer, et al., The Economic Costs of Disease Related Malnutrition, Clinical Nutrition, 2013, 32:136-141.
Gezondheidsraad Ondervoeding bij ouderen (Health Council of the Netherlands Malnutrition in the Elderly) Health Council of the Netherlands, Nov. 29, 2011.

(Continued)

*Primary Examiner* — Thomas S Heard

(74) *Attorney, Agent, or Firm* — Nixon & Vanderhye, P.C.

(57) ABSTRACT

The present invention relates to novel liquid or semi-liquid nutritional compositions, and powders to generate such liquid or semi-liquid nutritional compositions, that are beneficial in the treatment of malnutrition and malnutrition-related disorders such as weight loss and muscle wasting. When administered regularly, the nutritional compositions according to the present invention contribute to the reversal of malnutrition and malnutrition-related disorders such as weight loss and/or muscle atrophy.

10 Claims, 6 Drawing Sheets

(56) References Cited

OTHER PUBLICATIONS

"Tackling Malnutrition: Oral Nutritional Supplements as an Integrated Part of Patient and Disease in Hospital and in the Community. A Summary of the Evidence Base" Prepared on behalf of Medical Nutrition International Industry, Jul. 2010.
Dutch Search Report dated Jun. 26, 2015, which issued during prosecution of Dutch Application No. 2015032.
International Search Report and Written Opinion of the International Searching Authority dated Sep. 7, 2016, which issued during prosecution of International Application No. PCT/EP2016/064636.
Kunkel, S.D., et al., "mRNA Expression Signatures of Human Skeletal Muscle Atrophy Identify a Natural Compound that Increases Muscle Mass" Cell Metabolism, Mar. 2011, 13(6):627-638.
Li, Ying, et al., "Ursolic Acid Stimulates Lipolysis in Primary-Cultured Rat Adipocytes," Mol. Nutr. Food Res., 2010, 54, 1609-1617.
Milne, A.C. et al., "Protein and Energy Supplementation in Elderly People at Risk from Malnutrition." Cochrane Database of Systematic Reviews 2009, Issue 2.
Rao, Vietla S., et al., "Ursolic Acid, a Pentacyclic Triterpene from Sambucas Australis, Prevents Abdominal Adiposity in Mice Fed a High-Fat Diet," Journal of Food Medicine, 14 (11) 2011, 1375-1382.
Van Kan, G. Abelian, et al., "Gaid Speed at Usual Pace as a Predictor of Adverse Outcomes in Community-Dwelling Older People an International Academy on Nutirtion and Again (IANA) Task Force," The Journal of Nutrition, Health & Aging, vol. 13, No. 10, 2009.
Tripkovic, Laura et al., "Corparision of Vitamin D2 and Vitamin D3 Supplementation in Raising Serum 25-hydroxyvitamin D Status: A Systematic Review and Meta-Analysis," American Journal Clinical Nutrition, 2012, 95:1357-1364.
Deutz, Nicollas E.P., et al., "Muscle Protein Synthesis in Cancer Pateints can be Stimulated with a Specially formulated Medical Food," Clinical Nutrition 30, 2011, 759-768.
Rasmussen, Chirstopher J., et al., "Nutritional Supplements for Endurance Athletes," Nutritional Supplements in Sports and Exercise, 2014, pp. 370-407.
Calvani, Riccardo et al., "Current Nutritional Recommendations and Novel Dietary Stragegies to Manage Sacropenia," Journal of Frailty Aging, 2013: 2(1): 38-53.
Notice of Opposition against EP3313207 in the Name of Vitalnext B.V. dated Sep. 10, 2020.
MacDonald, H., et al. "Comparison of vitamin D2 and vitamin D3 supplementation in increasing serum 25-hydroxyviutamin D status: a systematic review and meta-analysis," Letters to the Editor, The American Journal of Clinical Nutrition, vol. 96, Issue 5, Nov. 2012, pp. 1152-1153.
Unknown "Membership of Scientific Advisory Committee on Nutrition: Working Group on Vitamin D," Vitamin D and Health, Scientific Advisory Committee on Nutrition (SACN), Jul. 2016.
Unknown "Converting Units of Measure for Folate, Niacin, and Vitamins A, D, and E on the Nutrition and Supplement Facts Labels: Guidance for Industry", U.S. Department of Health and Human Services, Food and Drug Administration, Center for Food Safety and Applied Nutrition, Aug. 2019; available at https://www.fda.gov/FoodGuidances.
Unknown, Product information sheet of Nutridrink Compact Protein, Aug. 2014.
Unknown, Product information sheet of Nutridrink Compact Protein, Jul. 2015; https://www.nutricia.dk/wpcontent/oloads/207/11/Nutridrink_Compact_Protein_2015-1.pdf.
Unknown, Product information sheet of Forticare.
Unknown, Product information sheet of Forticare; https://www.nutricia.co.za/upload/product%20pdfs/Forticare_cappuccino%20Fact%20Sheet%20SA.pdf, May 2016.
Van Den Hoek, A., et. al., "A novel nutritional supplement prevents muscle loss and accelerates muscle mass recovery in caloric-restricted mice," Metabolism Clinical and Experimental, 97:57-67, 2019.
Grootswagers, P., et al., "A novel oral nutritional supplement improves gait speed and mitochondrial functioning compared to standard care in older Adults with (or at risk of) undernutrition: Results from a randomized controlled trial" Aging, vol. 13, Advance, 2021.
Vandewoude, M.F.J., et al. "Malnutrition-Sarcopenia syndrome: Is future of nutrition screening and assessment for alder adults" Journal of Aging Research, vol. 2012 (3), Sep. 2012.
Tisdale, M.J., "Mechanisms of Cancer Cachexia" Physiological Reviews, 89:381-4010, 2009.
Anker, M.S., et al. "Highlights of mechanistic and therapeutic cachexia and sarcopenia research 2010 to 2012 and their relevance for cardiology" Arch. Med. Sci. 2013; 9 (1): 166-171.
Adams, C.M., et al. "Use of mRNA expression signatures to discover small molecule inhibitors of skeletal muscle atrophy" Current Opinion Clinical Nutr. Metab. Care, May 2015; 18 (3):263-8.
Ceglia, L., "Vitamin D and skeletal muscle tissue and function" Molecular Aspects of Medicine, 29 (2008) 407-414.
Unknown, Annex I (clinical study) to Response to the Communication pursuant to Rules 161(1) and 162 filed in related EP Appl. No 16734598.2 dated Jan. 8, 2018.
Mijnarends et al., J Nutr Health Aging 22(7):766-773 (2018).
Li et al., World J Gastroenterol. 8(3): 493-495 (2002).
Cardenas et al., Biochem Biophys Res Comm 320:402-408 (2004).
Ikeda et al., Mol. Nutr. Food Res. (2008) 52: 26-42 (2008).
Kim Min-Jung et al., Intl J Oral Biology 36: 7-11 (2011).
Xiong et al., Journal of Chinese Medicinal Materials 26: 578-581 (2003).
Liobikas et al., J. Nat. Prod. 74: 1640-1644 (2011).
Shan et al., Chinese Journal of Integrative Medicine 17: 607 (2011).

* cited by examiner

| Body weight: p-value | | t=0 | t=1 | t=2 | t=3 | t=4 | t=5 | t=6 |
|---|---|---|---|---|---|---|---|---|
| Chow reference vs: (non-starved) | Control, chow 100% | 0,001 | 0,001 | 0,001 | 0,001 | 0,001 | 0,001 | 0,001 |
| | Nutridrink | 0,001 | 0,001 | 0,001 | 0,001 | 0,003 | 0,013 | 0,005 |
| | Vital01 | 0,001 | 0,001 | 0,001 | 0,019 | 0,206 | 0,859 | 0,513 |
| Control, chow 100% vs: | Nutridrink | 0,529 | 0,971 | 0,912 | 0,353 | 0,247 | 0,190 | 0,315 |
| | Vital01 | 0,481 | 0,315 | 0,143 | 0,002 | 0,001 | 0,001 | 0,001 |
| Nutridrink vs: | Vital01 | 0,912 | 0,481 | 0,143 | 0,019 | 0,023 | 0,009 | 0,011 |

Fig. 11

| Tissue weight: p-value | | Quadriceps | | | Gastrocnemius | | |
|---|---|---|---|---|---|---|---|
| | | Left (g) | Right (g) | AVG (g) | Left (g) | Right (g) | AVG (g) |
| Chow baseline vs: (prior to starvation phase) | Chow reference | 0,841 | 0,151 | 0,421 | 0,032 | 0,841 | 0,222 |
| | Muscle wasting group | 0,001 | 0,001 | 0,001 | 0,001 | 0,001 | 0,001 |
| | Control, chow 100% | 0,003 | 0,001 | 0,001 | 0,001 | 0,001 | 0,001 |
| | Nutridrink | 0,001 | 0,001 | 0,001 | 0,001 | 0,001 | 0,001 |
| | Vital01 | 0,005 | 0,001 | 0,001 | 0,001 | 0,008 | 0,003 |
| Chow reference vs: (non-starved) | Muscle wasting group | 0,001 | 0,003 | 0,001 | 0,001 | 0,001 | 0,001 |
| | Control, chow 100% | 0,001 | 0,001 | 0,001 | 0,001 | 0,001 | 0,001 |
| | Nutridrink | 0,001 | 0,001 | 0,001 | 0,001 | 0,001 | 0,001 |
| | Vital01 | 0,001 | 0,001 | 0,001 | 0,013 | 0,005 | 0,003 |
| Muscle wasting group vs: | Control, chow 100% | 0,005 | 0,123 | 0,023 | 0,063 | 0,089 | 0,089 |
| | Nutridrink | 0,007 | 0,029 | 0,009 | 0,052 | 0,165 | 0,075 |
| | Vital01 | <0.001 | 0,011 | <0.001 | 0,019 | 0,002 | 0,004 |
| Control, chow 100% vs: | Nutridrink | 0,684 | 0,393 | 0,912 | 0,739 | 0,912 | 0,739 |
| | Vital01 | 0,123 | 0,063 | 0,043 | 0,280 | 0,023 | 0,105 |
| Nutridrink vs: | Vital01 | 0,015\* | 0,143 | 0,075 | 0,190 | 0,007\* | 0,043\* |

COMPOSITIONS AND METHODS FOR THE TREATMENT OF MALNUTRITION

RELATED APPLICATIONS AND INCORPORATION BY REFERENCE

The present patent application is a divisional of U.S. application Ser. No. 15/738,215 filed Dec. 20, 2017, which is a U.S. National Phase Application of International Patent Application No. PCT/EP2016/064636 filed Jun. 24, 2016, claiming the benefit of priority to Dutch Patent Application No. 2015032 filed Jun. 25, 2015, the contents of each of which are herein incorporated by reference in their entirety.

FIELD OF THE INVENTION

The invention relates to the field of medicine and nutrition. More in particular, the invention relates to means and methods for the treatment of malnutrition that may be the result of a disease. The invention further relates to nutritional compositions for enteral administration, and supplements, and particular combinations of compounds in such nutritional compositions and supplements, to treat patients suffering from malnutrition and complications related thereto, such as loss of body weight and muscle atrophy.

BACKGROUND ART

Malnutrition is a state of nutrition in which a deficiency, excess or imbalance of energy, protein, and other nutrients causes measurable adverse effects on tissue/body form (body shape, size and composition), function, and clinical outcome (Stratton R J et al. 2003. Disease-related malnutrition: an evidence based approach to treatment. Wallingford: CABI Publishing). With an ageing population around the globe, disease related malnutrition is a growing phenomenon and increasing public health concern. In Europe alone, approximately 33 million patients suffer from disease or age-related malnutrition (Ljungqvist O et al. 2010. The European fight against malnutrition. *Clin. Nutr* 29:149-150). Malnutrition affects all age groups, but older people are particularly at risk: the risk of malnutrition is 40% greater in people aged over 65 than in people aged below 65. It has been determined that hospitalized people are particularly at risk: one in four patients admitted to hospitals are at risk of malnutrition or are already malnourished, and up to 90% of residents in long-term care are at risk. Malnutrition is also common across a variety of patient groups and is particularly prevalent in people with cancer or AIDS. Malnutrition is caused primarily by poor food and nutrient intake and/or uptake; the effects of disease and treatment may further contribute to the development of malnutrition. Hospitalized patients often fail to meet their daily need for energy, protein and micronutrients. Through this, it increases complication rates, morbidity, mortality, hospital readmission and length of hospital stay. Disease related malnutrition adversely impacts every organ system in the body with potentially serious consequences on a physical and psycho-social level contributing to increased morbidity and mortality (Elia M and Russell C. 2009. Combating malnutrition: recommendations for action. Report from the Group on Malnutrition. Led by British Association of Parenteral and Enteral Nutrition, BAPEN, Redditch). Obviously, the increase in malnutrition cases results in higher treatment costs and associated costs to the society. Despite the apparent problems related to malnutrition, and that direct and indirect costs related to malnutrition are significant, it remains often overlooked, undetected and untreated. Hence, there is a constant need for monitoring malnutrition and methods and means to detect, and to treat malnutrition and the severe effects that it often results in.

Malnutrition affects the function and recovery of every organ system including the immune system, gastro-intestinal and cardio-respiratory functions, but primarily and mostly impairs muscle mass and function. Weight loss due to depletion of fat and muscle mass, including organ mass, is often the most obvious sign of malnutrition. Muscle function declines before changes in muscle mass occur, suggesting that altered nutrient intake has an important impact independent of the effects on muscle mass. Similarly, improvements in muscle function with nutrition support occur more rapidly than can be accounted for by replacement of muscle mass alone (Stratton R J et al. 2003. Disease-related malnutrition: an evidence based approach to treatment. Wallingford: CABI Publishing; Green C J 1999. Existence, causes and consequences of disease-related malnutrition in the hospital and the community, and clinical and financial benefits of nutrition intervention. Clin Nutr 18:3-28). Down-regulation of energy dependent cellular membrane pumping, or reductive adaptation, is one explanation for these findings. This may already occur following only a short period of starvation. If, however, dietary intake is insufficient to meet requirements over a more prolonged period of time, the body draws on its own functional reserves in tissues and starts breaking down skeletal muscle tissue for supply of amino acids, and glucagon stores and fat tissue to obtain sufficient energy. Decreased muscle mass often leads to decreased physical activity, further amplifying the detrimental effects of malnutrition on muscle mass and function. Reduction in cardiac muscle mass is also observed in malnourished individuals, leading to decreased cardiac output and a corresponding impact on renal function by reducing renal perfusion and glomerular filtration rate. In addition, impaired respiratory and diaphragmatic muscle function reduces cough pressure, leading to difficulties in expelling the lungs from secretions, and delaying recovery from respiratory tract infections.

Adequate nutrition is also important for preserving gastro-intestinal function: chronic malnutrition results in changes in pancreatic and bladder exocrine functions, intestinal blood flow, villous architecture and intestinal permeability. The colon loses its ability to reabsorb water and electrolytes, and secretion of ions and fluid occurs in the small and large bowel. This may result in diarrhea, which is associated with an even higher mortality rate in already weakened, malnourished patients.

Lack of sufficient nutrients has further been described to delay wound healing in malnourished surgical patients and to negatively affect the immune system, thereby increasing the risk of infection due to impaired cell-mediated immunity and cytokine, complement and phagocyte function. In addition to these physical consequences, malnutrition also results in psychosocial effects such as apathy, depression, anxiety and self-neglect, further worsening the disease progress.

One of the drawbacks of the nutritional compositions of the known art is that many of such supplements, or such functional foods, are composed of compounds that in itself may attribute to a better health, but for which it is unknown what the short term and long term effects are on reversing malnutrition. Supportive scientific data is generally lacking (or unpublished). Moreover, many of the ingredients in compositions of the known art are generally available food stuffs that may be combined and offered for sale without any restrictions in terms of governmental approval, and without any requirements of scientific data that would back up the claimed positive effects. There is a strong need for nutritional compositions that are effective in the treatment of malnutrition, wherein the effects on malnutrition are supported by sound scientific data, and not solely based on general thoughts on what may or may not be considered 'healthy'.

SUMMARY OF THE INVENTION

One of the objects of the invention is to provide new nutritional compositions that may be used to treat malnutrition and that cause increase in body weight and/or reverse the devastating effects of muscle atrophy, wherein such compositions are tested in scientific sound experiments and conclusions in respect of their effects are based on significant scientific data.

A first aspect of the invention provides a liquid or semi-liquid nutritional composition comprising: 70 to 200 mg/ml dairy proteins, 30 to 45 ng/ml vitamin D or a derivative thereof; and 0.2 to 0.8 mg/ml ursolic acid; wherein the casein:whey ratio in said dairy proteins ranges from 20:80 to 80:20 and wherein 30 to 45% of the total amino acid content is a mixture of leucine, isoleucine and valine. In a preferred embodiment (or embodiments), the casein:whey ratio is about 60:40, and/or composition of the invention is substantially free of other proteins besides casein and whey, and/or the concentration dairy proteins is about 100 mg/ml, and/or the concentration ursolic acid is about 0.35 mg/ml, and/or the concentration vitamin D or a derivative thereof is about 37.5 ng/ml.

The invention also relates to a liquid or semi-liquid nutritional composition comprising the constituents with their respective concentrations as listed in Table II as disclosed herein, and further comprising 0.2 to 0.8 mg/ml ursolic acid.

The invention also relates to a powder formulation comprising dairy proteins, vitamin D or a derivative thereof, ursolic acid and optionally an amino acid premix comprising free leucine, free isoleucine and free valine; all in suitable amounts that, when combined with a suitable carrier (such as water or another appropriate liquid or semi-liquid carrier), yields a liquid or semi-liquid nutritional composition according to the invention. In yet another embodiment, the invention relates to a powder formulation comprising an amino acid premix comprising free leucine, free isoleucine and free valine; vitamin D or a derivative thereof; and ursolic acid; all in suitable amounts that, when combined with a dairy protein-containing product, such as milk, quark, butter, yoghurt, etc. yields a liquid or semi-liquid nutritional composition according to the invention.

The invention also relates to a liquid or semi-liquid nutritional composition according to the invention, or a dry powder formulation according to the invention, for use in the treatment of a patient suffering from malnutrition, weight loss and/or muscle atrophy. As outlined in the specification, malnutrition in this case preferably refers to under-nutrition. The invention also relates to a powder formulation according to the invention in the manufacture of a medicament for the treatment of malnutrition, weight loss and/or muscle atrophy.

BRIEF DESCRIPTION OF THE DRAWINGS

These and other aspects of the invention are apparent from and will be elucidated with reference to the embodiments described hereinafter. In the drawings, the effects of the claimed subject matter is further substantiated.

FIG. 11 shows the statistic calculations employed for muscle mass measurements in all groups. It is important to stress that the increase in muscle mass in animals treated with Vital01 is significantly better than the comparator Nutridrink CP (indicated in the table by an asterisk).

DETAILED DESCRIPTION OF EMBODIMENTS

Figures 1, 2:
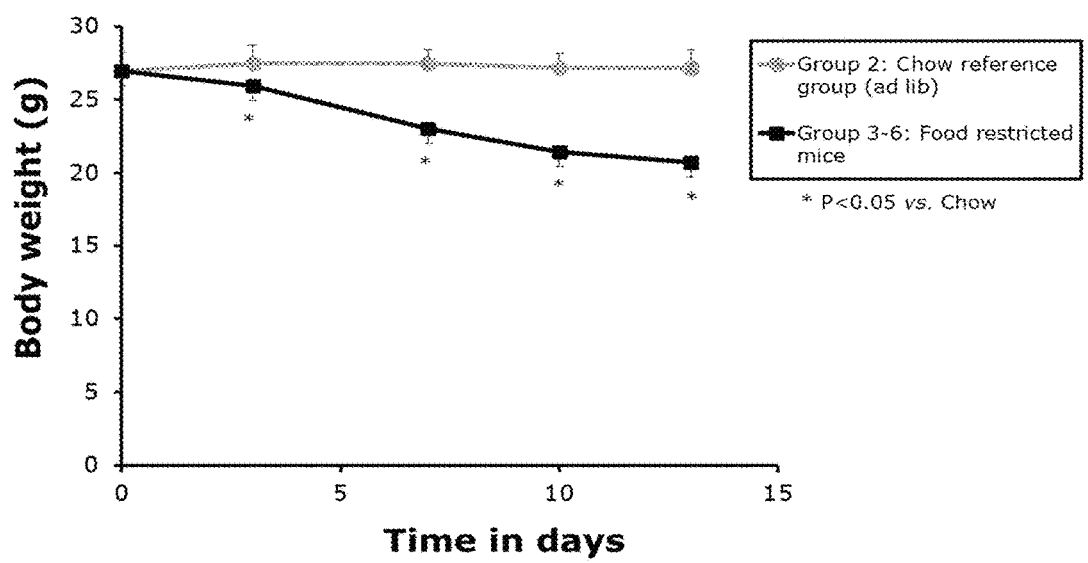
FIG. 1 shows the schematic outline of the study design of the starvation-refeeding experiment of example 1. In this study, animals were provided with a restricted diet (60% of normal daily intake) for a certain amount of time (starvation phase) to induce a state of malnutrition, in which the animals had lost approximately 25% of their bodyweight. In the following refeeding phase, restricted diets were supplemented with either regular mouse feed ("chow") up to their normal (100%) intake levels, or with equivalent amounts of the existing medical nutrition product Nutridrink Compact Protein (Nutridrink CP, Nutricia, the Netherlands) or the novel composition of the present invention, referred to as Vital01. Non-starved animals, maintained on a regular 100% chow diet served as control group for this study. From the start of the refeeding phase, daily measurements for total bodyweight and lean body mass were performed for all groups. The end of the study (e.o.s.) was defined as the day at which the first animals in any of the refeeding groups reached normal body weight, i.e. the average body weight of non-starved control animals. Baseline or reference samples were collected at relevant time point: the beginning of the study, at the end of the starvation phase, and at the end of study. Shown are the different groups within the experiment with their respective number of animals, the experimental timeline, and the refeeding composition that was provided. In the lower panel an 'x' indicates what action was taken on that particular study day. t=0 is the first day of the starvation period during which Groups 3-6 were limited in their daily energy intake to 60% of their regular intake (regular food intake was determined in the two preceding weeks before starvation) as indicated by the thick arrow. This period lasted two weeks and included day 13 (t=13). On day 14 (t=14) refeeding started for Groups 4-6. The control animals in Group 1 were sacrificed on day 1 (t=1) to obtain baseline levels for mass, weight and muscle characteristics. Control animals in Group 2 were maintained on a regular, 100% diet during the whole study and were sacrificed at the end of the study (t=e.o.s.) to obtain reference values for body weight and muscle characteristics. To study the effects of starvation on body weight and muscle characteristics, animals in Group 3 were sacrificed on day 14 at the end of the starvation period.
FIG. 2 shows the decline in total body weight of the mice, averaged for all animals in Groups 3-6 (that were maintained on the 60 kcal % diet for two weeks) in comparison to non-starved animals in control Group 2 (receiving their regular, daily 100 kcal % intake). On day 13 the mice had lost approximately 25% of their total body weight in all starvation groups. Shown is also that this weight loss was significant (P value <0.05).

Good nutrition is a vital part of care. Good nutritional care encompasses nutritional screening to identify patients at nutritional risk, and care planning to ensure that patients receive the right nutrition, at the right time. Nutritional intervention takes many forms from providing appetizing, nutritious food, to helping people eat and drink to providing tailored artificial nutrition support.

'Malnutrition' as used herein is defined as a state of nutrition in which a deficiency, excess or imbalance of energy, protein, and other nutrients causes measurable adverse effects on tissue/body form (body shape, size and composition), function, and clinical outcome. Although this definition in general relates both to over-nutrition (overweight/obesity) and under-nutrition, the methods and means of the present invention predominantly and most preferably are applied to treat under-nutrition. In other words, malnutrition as used herein refers to under-nutrition. Malnutrition further encompasses the additional concept of nutritional risk, reflecting common practice whereby these terms are often used interchangeably.

'Medical nutrition' is a term used to describe (commercially) available products for nutritional support, including oral nutritional supplements (ONS, see definition below), enteral tube feeds and parenteral nutrition. Medical nutrition fulfills the patient's nutritional requirements that are generally not met by the normal diet. It influences the immunological, biochemical, and metabolic status of the patient and thereby provides significant clinical benefits. Preferably, ONS use food-based ingredients with well-established safety records, and are in accordance to the European FSMP guidelines (Foods for Special Medical Purposes).

'Enteral nutrition' as used herein generally refers to any method of feeding that uses the gastrointestinal tract to deliver part or all of a person's caloric and nutrient requirements. It can include a normal oral diet, the use of oral nutritional supplements or delivery of part or all of the daily requirements through tube feeding via different routes such as nasoenteric, nasogastric, nasoduodenal, nasojejunal, rectal or through percutaneous tubes.

'Nutritional assessment' refers to a detailed, more specific and in-depth evaluation of a patient's nutritional state, typically by an individual/clinician with nutritional expertise (e.g. a dietitian, clinician studying nutrition, or a nutrition nurse specialist) or by a nutritional support team. This will usually be conducted in the case of nutritional problems identified by the screening process or when there is uncertainty about the appropriate course of action. The assessment process allows more specific nutritional care plans to be developed for the individual patient. Preferably, in accordance to the present invention, nutritional assessment includes the assessment of the patient's state or risk in respect of muscle atrophy, for which specified treatments may be required. Indicative of a malnutrition are for instance the occurrence of a low body mass index (BMI), unintentional weight loss, loss of appetite and food intake that appears insufficient to meet the average and normal requirements. Poor muscle strength and/or atrophy are also indicative for malnutrition or for nutritional intervention.

When malnutrition is noticed, generally such is followed by a care program that includes a range of activities including nutritional screening, care planning, nutritional interventions (food, ONS, tube and/or parenteral feeding) and follow-up designed to ensure that the patient's nutritional needs are evaluated, met and regularly reviewed. Severe malnutrition (severe under-nutrition) is generally clinically obvious. Nevertheless, there may be uncertainty about recognizing lesser degrees of malnutrition and events that occur as a consequence of malnutrition, such as muscle atrophy and other malnutrition-related diseases and disorders. In the absence of universally accepted criteria for identifying malnutrition with high sensitivity and specificity, the concept of nutritional risk is invoked. Risk is a measure of likelihood that malnutrition and/or muscle atrophy is present or likely to develop. It also reflects the risk of poor outcome as a result of impaired nutritional status. A patient that suffers from malnutrition and malnutrition-related disorders such as loss of body weight and/or muscle atrophy, are generally referred to as human subjects suffering from malnutrition (and/or muscle atrophy) that are in need of treatment. Nutritional screening is a rapid, simple and general procedure used by nursing, medical or other staff, to detect those at risk of suffering from nutritional problems, so that action can be taken, preferably by administering the compositions of the present invention, or in another aspect, by providing the treatment methods as disclosed herein. Screening should generally be repeated at intervals.

'Nutritional support' generally refers to support that includes food, ONS (such as those of the present invention), tube feeding and parenteral nutrition.

'Oral nutritional supplements' (ONS) as used herein, are multi-nutrient liquid, semi-solid, semi-liquid or powder products (that may be dissolved to form a (semi-)liquid) that provide macronutrients and micronutrients, preferably with the aim of increasing oral nutritional intake and that add to the treatment of disorders, which have resulted from malnutrition (under-nutrition). Preferably, ONS are nutritionally complete and could preferably also be used as a sole source of nutrition. ONS are distinct from dietary supplements that provide vitamins, minerals and/or trace elements in a pill format (also known as food supplements). When producing compositions such as those of the present invention, one has to consider the European FSMP guidelines as outlined in Commission Directive 1999/21/EC of 25 Mar. 1999 on dietary foods for special medical purposes (as amended by Directive 2006/141/EC) that sets out rules for the composition and labelling of foods that are specifically formulated, processed and intended for the dietary management of diseases, disorders or medical conditions of individuals who are being treated under medical supervision. These foods are intended for the exclusive or partial feeding of people whose nutritional requirements cannot be met by normal foods. Of course, nutritional compositions of the present invention may comprise compounds and agents that are (or may be) present in certain and generally available dietary- and food supplements. In other words, the presence of a compound that is often administered as an ingredient of a dietary supplement or in a food-supplement (such as vitamins) does not make the nutritional compositions of the present invention a dietary supplement or a food supplement.

It should be understood that the definition 'semi-liquid' refers to a substance that is flowing, but may be slow-flowing like a syrup, or having a soft texture like quark or (soft) butter, or a firm milkshake. In any case, a liquid or semi-liquid nutritional composition according to the invention can be administered via enteral routes, preferably orally, and in a suitable form, perhaps even at the patient's request in a form that the patient prefers.

It is generally considered that providing an ONS is an effective strategy for the management of malnutrition in hospitalized patients, older people and people who are undernourished. It has been shown to improve nutritional intake, increase or attenuate weight loss and improve function or activities of daily living. Nevertheless, it has also been found that the intake of ONS suffer from poor adherence (also referred to as 'compliance'), a term used to describe how well a patient is following the advice or treatment plan. Reasons for such poor adherence are varied. For instance, many medical nutrition formulations are simply tasteless or have a taste that is considered as 'bad' by many. Another aspect adding to poor compliance is slow gastric emptying and the high level of satiety that individuals experience after taking a serving of currently available medical nutrition formulations. Poor food and nutrient intake due to disability are at the heart of the cause of malnutrition, for example patients with cancer may have altered taste, nausea and anorexia due to treatment; patients with stroke or other neurological conditions may have swallowing difficulties or problems with self-feeding. Other causes are confusion, low mood and anxiety disturbances, chewing and swallowing problems, pain, vomiting, feeling full rapidly, lack of alertness, dry mouth, constipation, poverty, self-neglect, dementia, deprivation and poor food choices. The key physical and psycho-social consequences of malnutrition are impaired immune responses, impaired muscle strength and fatigue, inactivity, impaired temperature regulation, impaired wound healing, impaired ability to regulate electrolytes and fluids and impaired psycho-social functioning. Severe inactivity and impaired muscle strength is often seen in patients that cannot leave their beds. A well-known result of being bedridden for prolonged period of time is muscle decay, the wasting of muscle, generally referred to as 'muscle atrophy'. Starvation (severe malnutrition) and disuse of muscles eventually always leads to muscle atrophy. Hence, although a patient may or may not have proper nutritional intake, the fact that the patient is bedridden and is unable to exercise sufficiently, may result in- and will certainly add to the appearance of muscle atrophy. The present invention provides methods and means to counteract and/or prevent muscle atrophy, either due to malnutrition, and/or due to prolonged disuse of muscles, for instance in the case of patients that need to stay in bed and cannot use their muscles sufficiently. The nutritional compositions of the present invention have a protein composition that generally ensures a more rapid release from the stomach than products known in the art, predominantly due to the high whey content. High casein content makes that under low pH circumstances, such as in the stomach, the product hardens and precipitates. The relative higher abundance of whey protein in the nutritional compositions of the present invention causes a lower precipitation in the stomach and a more rapid entry into the gut. This effect makes that people tend to feel less 'full' after taking the nutritional compositions of the present invention, as compared to nutritional supplements from the art that have a high casein content and a low whey content. Feeling less 'full' ensures a better compliance.

Muscle atrophy is a widely known and widespread disorder. Compositions that counteract muscle atrophy are known. For instance, US 2006/0035824 (A1) discloses the administration of gOBG3, thereby accelerating the reorganization and differentiation of muscle cells, and thereby treating the muscle disorder.

Notably, the present invention relates to a composition that appears unique and highly beneficial in the treatment of weight loss and malnutrition-related muscle atrophy, when compared to the ONS known in the art. Such is outlined in detail in the accompanying examples below. One of the preferred ingredients in the compositions of the present invention is 'ursolic acid' with the chemical formula $C_{30}H_{48}O_3$, which is sometimes referred to as urson, prunol, malol, 3-3-hydroxy-urs-12-ene-28-oic acid or 3-beta-3-hydroxy-urs-12-ene-28-oic-acid. Ursolic acid belongs to the family of pentacyclic triterpenoids that also includes its isomers like oleanolic acid, and all of its natural occurring analogs and derivatives such as glycosides. It is found in many herbs, plants and fruits, such as basil, cranberries, and rosemary. Especially apple peels contain relatively high quantities of ursolic acid. As such, ursolic acid in low concentrations can be considered a common constituent of the human diet. Ursolic acid has been ascribed several roles including anti-tumor effects by inhibiting the STAT3 activation pathway. It is thought to prevent cancer cell proliferation and induce apoptosis. Ursolic acid has also been found to inhibit JNK expression and IL-2 activation of Jurkat leukemic T cells leading to the reduction of proliferation and T cell activation. The use of ursolic acid for the treatment of muscle atrophy has been suggested (Kunkel S D et al. 2011. mRNA expression signatures of human skeletal muscle atrophy identify a natural compound that increases muscle mass. Cell Metab 13(6):627-638). Furthermore, WO 2012/170546 discloses the use of at least seven compound classes including thousands of derivatives thereof to treat muscle atrophy. Ursolic acid has also been disclosed for use against Alzheimer's disease (U.S. Pat. No. 8,021,701).

The compositions of the present invention have a casein to whey protein ratio ranging from 20:80 to 80:20. Nutridrink CP (as shown in the examples) has a casein to whey ratio of approximately 93:7. Preferably, all protein in the compositions of the present invention are dairy proteins. In other aspects of the invention the dairy casein and whey proteins may be supplemented with protein from other animal or plant sources. The term 'casein' as used herein refers both to caseinate and micellar casein. The caseinate may be sodium-caseinate, calcium-caseinate, magnesium-caseinate, or potassium-caseinate. Preferably, the caseinate is calcium-caseinate or sodium-caseinate. Whey protein is a superior class of food protein. It has a good amino acid profile and it is known to increase protein synthesis in mammals (due to its high leucine content). Whey protein is well-tolerated and as mentioned above, it ensures increased gastric emptying. Moreover, whey protein has bioactive proteins with immune enhancing properties (lactoglobulins, α-lactalbumin, immunoglobulins, lysozyme, and lactoferrins).

The present invention relates to a liquid or semi-liquid nutritional composition comprising: 70 to 200 mg/ml dairy proteins; 30 to 45 ng/ml vitamin D or a derivative thereof; and 0.2 to 0.8 mg/ml ursolic acid; wherein the casein:whey ratio in said dairy proteins ranges from 20:80 to 80:20 and wherein 30 to 45% of the total amino acid content is a mixture of leucine, isoleucine and valine. In a preferred embodiment, the casein:whey ratio in said liquid or semi-liquid nutritional composition is about 60:40, and/or the concentration dairy proteins is about 100 mg/ml, and/or the concentration ursolic acid is about 0.35 mg/ml. As disclosed herein, the amount of dairy proteins that was used was approximately 10.56 g/100 ml, which includes a small percentage of fat. For this the preferred amount of dairy proteins is set at 100 mg/ml. It should be noted that the amount of dairy proteins may range between 70 to 200 mg/ml in the composition to yield good results in the treatment of malnutrition, weight loss and/or muscle atrophy. In another preferred embodiment, the composition is substantially free of other proteins besides casein and whey. This means that in a preferred aspect of the present invention the casein protein+whey protein adds up to 100% of the protein amount. For example, when the amount of protein from casein is 60%, then the remainder of the protein content is preferably 40%, all from whey protein. The nutritional compositions of the invention preferably comprises a mixture of free branched-chain amino acid selected from the group consisting of leucine, isoleucine and valine. These amino acids are the only three branched-chain proteinogenic amino acids present in nature, and all three are essential amino acids for humans. However, in the event that sufficient dairy proteins are present in the composition of the present invention in which 30-45% of the total amino acid content in said composition is made up of a mixture of leucine, isoleucine and valine, no additional (free) amino acids of these types are required. However, when the dairy protein content is such that the range of 30-45% of these essential amino acid mix is not reached, free amino acids of this type will be added, preferably in a premix. The amounts of the three amino acids as listed in Table II are preferred. The minimal preferred concentration of isoleucine is 7%, the minimal preferred concentration of valine is 7% and the minimal concentration of leucine is 16%, all of the total amino acid content in the composition (=30%). A preferred range to yield 45% is 10% isoleucine, 10% valine and 25% leucine. Hence, in a preferred aspect, the invention relates to a liquid or semi-liquid nutritional composition according to the invention, comprising valine and isoleucine both in a concentration of 7 to 10% of the total amino acid content and leucine in a concentration of 16 to 25% of the total amino acid content, and wherein valine, isoleucine and leucine are present in both free and bound form. Most preferably, isoleucine and valine are both present in a concentration of 8% of the total amino acid content, whereas isoleucine is then present in a concentration of 20% of the total amino acid content. In yet another preferred embodiment, the liquid or semi-liquid nutritional composition of the present invention also comprises Vitamin D, preferably in a concentration of about 37.5 ng/ml. It is known in the art that there are two types of Vitamin D, both considered herein as 'derivatives of Vitamin D':Vitamin D2 and Vitamin D3, which may both (solely or in combination) be part of the nutritional composition of the present invention. Preferably Vitamin D3 is used.

For transportation, handling and storage it is highly preferred to have nutritional composition mixtures in powder form that may be dissolved, dispersed or otherwise mixed in a suitable solvent (such as water or any other suitable carrier) just before administration. In a preferred embodiment, the present invention relates to a powder that, when dissolved in a suitable solvent, forms a liquid or semi-liquid composition suitable for enteral, preferably oral, administration, and wherein the amounts of the constituents in the powder are such that the correct amounts of ingredients are generated and that, preferably, a ⅙ daily dose is generated. Hence, the invention also relates to a powder formulation comprising dairy proteins, vitamin D or a derivative thereof, ursolic acid; and optionally an amino acid premix comprising free leucine, free isoleucine and free valine; all in suitable amounts that, when combined with a suitable carrier, yields a liquid or semi-liquid nutritional composition according to the invention. In yet another aspect the invention relates to a powder formulation comprising an amino acid premix comprising free leucine, free isoleucine and free valine, vitamin D or a derivative thereof; and ursolic acid; all in suitable amounts that, when combined with a dairy protein-containing product, such as milk, buttermilk, quark or yoghurt, yields a liquid or semi-liquid nutritional composition according to the invention. This may be for taste reasons or for other reasons such that the liquid or semi-liquid composition that results may be easily administered or swallowed. The person skilled in the art will have no problem calculating the correct amounts in the powder formulation to yield a liquid or semi-liquid nutritional composition as disclosed herein for suitable administration to a person or patient in need thereof. Clearly, when dairy products, such as milk, buttermilk, quark or yoghurt (or any other suitable milk-derived dairy product that the patient prefers) are used for dissolving or combining with the powder formulations of the present invention, the amounts, concentrations and/or percentages of dairy proteins therein can be easily calculated and the suitable amounts of the other constituents as disclosed herein can be added to yield a liquid or semi-liquid nutritional composition of the present invention. The powder formulation of the present invention is 'substantially dry', which means that trace amounts of a liquid (from the air or otherwise) may be present, but that the powder is free-flowing and in principle suitable for handling, dissolving, transportation and/or (long-term) storage.

In yet another aspect of the invention, the liquid or semi-liquid composition of the present invention is a dose of 100 ml wherein the compounds are dissolved or dispersed or taken up, preferably by a single dispersion of a powder according to the present invention in a suitable solvent to finally yield a nutritional composition according to the present invention. A 100 ml dose is suitable for oral administration and is generally suitable as a ⅙ daily dose. Preferably, the liquid in which the powder of the present invention is dissolved, is water. In yet another preferred aspect, the powder of the present invention comes in packages that can easily be used for dissolving the powder in a solvent. Hence, for a daily dose, 6 powder packages are provided that may each be dissolved separately, or as an alternative, a powder is provided that contains as much as a full daily dose, and after dissolving, may be consumed spread over a single day. It will be understood that different combinations in this may be offered, depending on the wishes and abilities of the subject consuming the composition of the present invention. In that case, the powder of the present invention may or may not contain dairy proteins as the required dairy proteins come from the solvent in which the powder is dissolved. In any event, the result will be a liquid or semi-liquid nutritional composition according to the invention. In conclusion, when a powder of the present invention is dissolved in a non-dairy protein containing solvent, the powder contains the dairy proteins in the amounts as disclosed herein. In the event that the powder of the present invention is dissolved in a solvent that already contains dairy proteins, the powder may lack dairy proteins, or may contain dairy proteins in such suitable amounts that the resultant is a liquid or semi-liquid nutritional composition according to the present invention and as used and disclosed herein. The skilled person would be able to determine the amount of dairy proteins such as casein and whey, determine their ratio, and based on that, determine the amount of dairy proteins to be added to the powder to achieve the correct amounts of dairy proteins when a liquid or semi-liquid nutritional composition according to the present invention is wanted. The same holds true for the concentrations of the essential amino acids leucine, isoleucine and valine, that may be present (all) in the dairy proteins, but that may also be added as free amino acids to reach the concentrations of the compositions of the present invention.

In another preferred embodiment, the invention relates to liquid or semi-liquid nutritional composition comprising the constituents with their respective concentrations as listed in Table II and further comprising 0.2 to 0.8 mg/ml ursolic acid. The amounts are generally dissolved to form a liquid or semi-liquid for enteral administration. Preferably, and in line with what has been indicated above, the amounts of Table II together with the suitable amounts of ursolic acid are dissolved to form a liquid or semi-liquid for enteral administration of about 100 ml, which is approximately ⅙ of daily portion to treat malnutrition, weight loss and/or muscle atrophy. For storage, handling and transport purposes, it is preferred for this composition that the nutritional compositions of the present invention are held in a substantially dry state, such as a powder formulation. 'Substantially' as used herein refers to a powder that can be easily handled, that is free-flowing and that generally does not stick to the container in which it is held. Hence, preferably the nutritional composition according to the invention is a substantially dry powder for dissolving it in a suitable solvent, preferably water (in which case the powder contains dairy proteins in the suitable concentrations). The skilled person is aware of methods to produce such powders of the given ingredients.

For administration through enteral routes, different types of liquids or semi-liquids may be used. The nutritional composition of the present invention, when available in powder form, is preferably dissolved, dispersed, or mixed in a suitable carrier such as water, tea, fruit or vegetable juice, a suitable buffer, gel, pudding or yoghurt to obtain a substance that can easily be administered via drinking or for instance via tube-feeding. Clearly, when the powder is dispersed in for instance yoghurt, or other milk products, additional proteins become part of the substance that is administered, see above. Notably, a suitable carrier may be selected by a user or consumer based on personal preference and may contain intrinsic amounts of protein, vitamins or other ingredients which are not accounted for in Table II. Hence, the present invention, in another embodiment, also relates to a liquid or semi-liquid composition for oral delivery in which the powder of the present invention is dissolved. Dissolving the powder formulation of the present invention may occur any time before consumption, such as directly before or before the composition is offered in a container such as a bottle or a tube, as long as it does not go off or gets rotten.

In yet another aspect, the invention relates to a liquid or semi-liquid nutritional composition according to the invention, or a dry powder formulation according to the invention, for use in the treatment of a patient suffering from malnutrition, weight loss and/or muscle atrophy. The invention also relates to a powder formulation according to the invention in the manufacture of a medicament for the treatment of malnutrition, weight loss and/or muscle atrophy.

Notably, malnutrition (under-nutrition), weight loss and muscle atrophy may be related in the sense that weight loss occurs because muscle are suffering from atrophy, but may also be unrelated. Weight loss may occur independently of malnutrition but may be due to muscle atrophy that is the result of another disorder than malnutrition. Also, weight loss may not be completely due to loss of muscle loss, or muscle atrophy. And, muscle atrophy may be the result of malnutrition, it may also be the result of non-use of muscles, not directly as a result of malnutrition, but for instance due to prolonged immobility. In another embodiment, muscle atrophy or weight loss may be unrelated to malnutrition but may be the result of another disorder/disease such as cancer or AIDS. Hence, the nutritional compositions of the present invention may be administered for the treatment of malnutrition-related disorders such as muscle atrophy, whereas it may also be used in muscle atrophy treatment that is not directly caused by malnutrition. In either case, the administration of the nutritional compositions of the present invention results in muscle weight gain, and hence in weight gain and reverses muscle atrophy. Most preferably however, the nutritional compositions of the present invention are used in the treatment of malnutrition and malnutrition-related disorders.

In yet another embodiment, the present invention relates to ursolic acid for use in the treatment of malnutrition, weight loss and/or muscle atrophy. And in another embodiment, the present invention relates to the use of ursolic acid in the manufacture of a medicament for the treatment of malnutrition, weight loss and/or muscle atrophy.

The present invention also relates to a method for the treatment of a mammalian subject suffering from malnutrition, weight loss and/or muscle atrophy, comprising the steps of administering a liquid or semi-liquid nutritional composition according to the invention to said mammalian subject; monitoring the rate of malnutrition of said mammalian subject, and/or the weight of said mammalian subject, and/or the rate of muscle atrophy in said mammalian subject; and optionally adjusting the amount of ursolic acid and/or a composition according to the invention to be administered. It is envisioned that if the weight gain or reversal of malnutrition and/or muscle atrophy is not sufficient enough, the amount of administered ursolic acid or composition according to the invention may be altered, and preferably higher than initially administered, depending on the outcome of the assessment of the mammalian subject receiving the administration. In all aspects of the present invention, the mammalian subject as mentioned herein is preferably a human subject. It was calculated by the inventors of the present invention that the amounts of constituents, as exemplified in Table II should preferably be administered to the mammalian subject six times per day, which is therefore the preferred regimen. However, depending on the subject to be treated, the severity of the weight loss, malnutrition and/or muscle atrophy, and the nature of the carrier, the dosing volumes and intervals may be increased or decreased.

In one embodiment, the nutritional composition of present invention further comprises carbohydrate in an amount from about 6 to about 20 grams per 100 Kcal of the composition, such as from about 7 to about 18.5, from about 8 to about 16, from about 9 to about 14.5, from about 10 to about 13, such as about 11 grams per 100 Kcal of the composition. Where the composition according to the invention is a liquid or semi-liquid composition, it may comprise carbohydrate in an amount from about 150 to about 480 mg/ml, such as from about 160 to about 440 mg/ml, from about 170 to about 400 mg/ml, from about 180 to about 360 mg/ml, from about 190 to about 320 mg/ml, from about 200 to about 280 mg/ml, and preferably from about 210 to about 270 mg/ml. Suitable carbohydrates used in the composition are monosaccharides, disaccharides, polysaccharides and oligosaccharides. In one embodiment the carbohydrates are selected from maltodextrin and sugars, where suitable sugars may be glucose, fructose, sucrose, maltodextrins.

In one embodiment, the composition of the present invention further comprises one or more fats in an amount from about 1.5 to about 5.5 grams per 100 Kcal of the composition, such as from about 2.5 to about 5.0, from about 3.5 to about 4.5, such as about 4.0 grams per 100 Kcal of the composition. Where the composition according to the invention is a liquid or semi-liquid composition, it may comprise one or more fats in an amount of from about 40 to about 140 mg/ml, such as from about 52 to about 132 mg/ml, from about 64 to about 124 mg/ml, from about 76 to about 116 mg/ml, such as from about 88 to about 108 mg/ml, such as about 96 mg/ml. Suitable fats are monounsaturated, polyunsaturated and saturated fats. In one embodiment the one or more fats are selected from the group consisting of milk fat and vegetable oils.

In one embodiment, the nutritional composition of present invention further comprises branched chain amino acids, leucine, isoleucine and valine in an amount from about 0.5 to about 3.0 grams per 100 Kcal of the composition, or from about 12 to about 72 mg/ml if the composition is a liquid or semi-liquid composition for leucine; from about 0.2 to about 2.0 grams per 100 Kcal of the composition or from about 4.8 to about 48 mg/ml if the composition is a liquid or semi-liquid composition for isoleucine; and from about from about 0.2 to about 2.0 grams per 100 Kcal of the composition or from about 4.8 to about 48 mg/ml if the composition is a liquid or semi-liquid composition for valine. In a preferred embodiment, the amount of leucine is from about 0.75 to about 2.0, preferably about 1.0 grams per 100 Kcal of the composition, or, if the composition is a liquid or semi-liquid, from about 18 to about 48 mg/ml, preferably about 24.7 mg/ml. In a preferred embodiment, the amount of isoleucine is from about 0.3 to about 1.0, preferably about 0.44 grams per 100 Kcal of the composition, or, if the composition is a liquid or semi-liquid from about 7.2 to about 24 mg/ml, preferably about 10.6 mg/ml. In a preferred embodiment, the amount of isoleucine is from about 0.3 to about 1.0 l, preferably about 0.45 grams per 100 Kcal of the composition, or, if the composition is a liquid or semi-liquid from about 7.2 to about 24 mg/ml, preferably about 10.8 mg/ml.

In one embodiment, the composition of the present invention further comprises Calcium, Chloride, Phosphorus, Iron, Iodine, Potassium, Copper, Magnesium, Manganese, Sodium, Selenium, Zinc, and/or salts thereof. In another embodiment, the composition further comprises Chromium, Molybdenum, and/or salts thereof. In yet another embodiment of the invention, the composition comprises Fluoride. In a highly preferred embodiment of the invention the composition comprises these elements in amounts complying with the regulations for compositions of medical nutrition, such as e.g. the Commission Directive 1999/21/EC of 25 Mar. 1999 in EU.

In one embodiment, the composition of the present invention further comprises vitamin C, vitamin E, vitamin A, vitamin B3, vitamin D, pantothenic acid, vitamin K1, vitamin B1, vitamin B6, vitamin B2, folic acid, biotin and vitamin B12. In a highly preferred embodiment of the invention the composition comprises these vitamins in amounts complying with the regulations for compositions of medical nutrition, such as e.g. the Commission Directive 1999/21/EC of 25 Mar. 1999 in EU.

In further embodiments, it is also possible to further add one or more of the following components selected from the list consisting of leucine metabolites such as 13-Hydroxy β-Methylbutyrate (HMB), glutamine, carnitine, beta-alanine, carnosine, creatine, bioactive peptides and omega-3 fatty acids such as EPA and DHA.

The different components of a nutritional composition according to the present invention can be varied within the given ranges for each component independently of one another. In certain situations an even more optimal effect can be achieved by choosing an optimum for a plurality of components in combination.

It should be noted that the above-mentioned embodiments illustrate rather than limit the invention, and that those skilled in the art will be able to design many alternative embodiments. In the claims, use of the verb "comprise" and its conjugations does not exclude the presence of elements or steps other than those stated in a claim. The article "a" or "an" preceding an element does not exclude the presence of a plurality of such elements.

Advantageous embodiments are set out in the following clauses. The Applicants hereby give notice that new claims may be formulated to such clauses and/or combinations of such clauses and/or features taken from the description, during prosecution of the present application or of any further application derived therefrom.

1. A liquid or semi-liquid nutritional composition comprising:
70 to 200 mg/ml dairy proteins;
30 to 60 ng/ml vitamin D or a derivative thereof; and
0.2 to 1 mg/ml ursolic acid;
wherein the casein:whey ratio in said dairy proteins ranges from 20:80 to 80:20 and
wherein 30 to 45% of the total amino acid content is a mixture of leucine, isoleucine and valine.

2. A liquid or semi-liquid nutritional composition according to clause 1, wherein the casein:whey ratio is from about 30:70 to about 70:30, such as from about 40:60 to about 68:32, from about 45:55 to about 65:35, such as about 60:40.

3. A liquid or semi-liquid nutritional composition according to any of clauses 1 or 2, wherein the casein:whey ratio is about 50:50.

4. A liquid or semi-liquid nutritional composition according to any of the preceding clauses, comprising from about 1.5 to about 3 Kcal/ml such as from about 1.8 to about 2.7 Kcal/ml or from about 2 to about 2.5 Kcal/ml 5. A liquid or semi-liquid nutritional composition according to any of the preceding clauses, wherein the composition is substantially free of other proteins besides casein and whey.

6. A liquid or semi-liquid nutritional composition according to any one of the preceding clauses, wherein the concentration of dairy proteins is from about 75 to about 180 mg/ml, such as from about 80 to about 160 mg/ml, from about 85 to about 140 mg/ml, from about 90 to about 130 mg/ml, from about 95 to about 125 mg/ml, from about 100 to a about 120 mg/ml, such as, about 100 mg/ml.

7. A liquid or semi-liquid nutritional composition according to any of the preceding clauses, wherein the concentration of ursolic acid is from about 0.2 to about 0.8 mg/ml, such as at about 0.35 mg/ml.

8. A liquid or semi-liquid nutritional composition according to any of clauses 1-6, wherein the concentration of ursolic acid is from about 0.25 to about 0.95 mg/ml, such as from about 0.3 to about 0.9 mg/ml or from about 0.35 to about 0.85 mg/ml, such as about 0.85 mg/ml.

9. A liquid or semi-liquid nutritional composition according to any of the preceding clauses, comprising valine and isoleucine in a concentration of 7 to 10% of the total amino acid content and leucine in a concentration of 16 to 25% of the total amino acid content, and wherein valine, isoleucine and leucine are present in free and bound form.

10. A liquid or semi-liquid nutritional composition according to any of the preceding clauses, wherein the concentration vitamin D or a derivative thereof is approximately 30 to 45 ng/ml.

11. A liquid or semi-liquid nutritional composition according to any of clauses 1-9, wherein the concentration vitamin D or a derivative thereof is from about 32 to about 55 ng/ml, from about 35 to about 45 ng/ml, such as approximately 37.5 ng/ml.

12. A liquid or semi-liquid nutritional composition that comprise the ingredients with their respective concentrations as provided in Table II and further comprises 0.2 to 0.8 mg/ml ursolic acid.

13. A powder formulation comprising
dairy proteins;
vitamine D or a derivative thereof;
ursolic acid; and
optionally an amino acid premix comprising free leucine, free isoleucine and free valine, in suitable amounts that when it is combined with a suitable carrier provides for a liquid or semi-liquid nutritional composition according to any of the preceding clauses.

14. A powder formulation according to clause 13, wherein the suitable carrier is water.

15. A powder formulation according to any of clauses 13 and 14, wherein a suitable amount of carrier is from about 1.5 to about 3 ml per gram of powder formulation, such as from about 1.7 to about 2.8 ml per gram of powder formulation.

16. A powder formulation according to any of clauses 13-15, wherein 100 grams of the powder comprises from about 300 to about 700 Kcal, such as, from about 350 to about 650 Kcal, from about 400 to about 600 Kcal or from about 450 to about 550 Kcal.

17. A powder formulation comprising
an amino acid premix comprising free leucine, free isoleucine and free valine;
vitamine D or a derivative thereof; and
ursolic acid;
in suitable amounts that when it is combined with a dairy-protein containing product such as milk or yoghurt, provides for a liquid or semi-liquid nutritional composition according to any one of clauses 1-12.

18. A nutritional composition comprising per 100 Kcal:
from about 2.5 to about 8.5 grams dairy proteins;
from about 1.2 to about 3.0 μg vitamin D or a derivative thereof; and
from about 8 to about 50 mg ursolic acid;
wherein the casein:whey ratio in said dairy proteins is from 20:80 to 80:20 and wherein 30 to 45% of the total amino acid content is a mixture of leucine, isoleucine and valine.

19. A nutritional composition according to clause 18, wherein the casein:whey ratio is from about 30:70 to about 70:30, such as from about 40:60 to about 68:32, from about 45:55 to about 65:35, such as about 60:40.

20. A nutritional composition according to any of clauses 18 or 19, wherein the casein:whey ratio is about 50:50.

21. A nutritional composition according to any of clauses 18-20, wherein the composition is substantially free of other proteins besides casein and whey.

22. A nutritional composition according to any of clauses 18-21, wherein the amount of dairy proteins is from about 3.0 to about 7.5, such as, from about 3.5 to about 6.5, from about 4.0 to about 6.0, or from about 4.5 to about 5.5, such as about 5.0 grams per 100 Kcal of composition.

23. A nutritional composition according to any of clauses 18-21, wherein the amount of ursolic acid is from about 15 to about 48, such as, from about 20 to about 46, from about 25 to about 44, from about 30 to about 40 or about 35 mg per 100 Kcal of composition.

24. A nutritional composition according to any of clauses 18-23, comprising valine and isoleucine in an amount of 7 to 10% of the total amino acid content and leucine in an amount of 16 to 25% of the total amino acid content, and wherein valine, isoleucine and leucine are present in free and bound form.

25. A nutritional composition according to any of clauses 18-24, wherein the amount of vitamin D or a derivative thereof is from about 1.6 to about 2.4, such as, from about 1.65 to about 2.2, such as from about 1.7 to about 2.0, such as, about 1.8 µg per 100 Kcal of composition.

26. A nutritional composition according to any of clauses 18-25, wherein the composition is a powder.

27. A liquid or semi-liquid nutritional composition according to any one of clauses 1-12, a powder formulation according to any one of clauses 13-17 or a nutritional composition according to any one of clauses 18-26, for use in the treatment of a patient suffering from malnutrition, weight loss and/or muscle atrophy.

28. A composition or formulation according to clause 27, wherein the patient is a human.

29. A composition or formulation according to any of clauses 27 and 28, wherein the liquid or semi-liquid nutritional composition is in a dosage of about $\frac{1}{7}$ to about $\frac{1}{5}$ of the daily energy intake of the patient.

30. A composition or formulation according to clause 29, wherein the liquid or semi-liquid nutritional composition is in a dosage of about $\frac{1}{6}$ of the daily energy intake of the patient.

31. A composition or formulation according to any of clauses 27-30, wherein the liquid or semi-liquid nutritional composition is in a dosage of about 200 to about 500 Kcal, such as of about 250 to about 350 Kcal, such as, about 300 Kcal.

32. A composition or formulation according to any of clauses 27-31, wherein the liquid or semi-liquid nutritional composition is in a dosage of about 100 to about 300 ml, such as, of about 150 to about 250 ml, such as, about 200 ml.

33. Use of a liquid or semi-liquid nutritional composition according to any one of clauses 1-12, a powder formulation according to any one of clauses 13-17 or a nutritional composition according to any one of claims 18-26, for treating, preventing or reducing malnutrition, weight loss and/or muscle atrophy in a mammalian subject.

34. Use according to claim 33, wherein the mammalian subject is a human.

35. Use according to any of clauses 33 and 34, wherein the composition or formulation is administered in a dosage of about $\frac{1}{7}$ to about $\frac{1}{5}$ of the daily energy intake of the subject.

36. Use according to clause 35, wherein the composition or formulation is administered in a dosage of about $\frac{1}{6}$ of the daily energy intake of the subject.

37. Use according to any of clauses 33-36, wherein the composition or formulation is administered in a dosage comprising about 200 to about 500 Kcal, such as, of about 250 to about 350 Kcal, such as, about 300 Kcal.

38. Use according to any of clauses 33-37, wherein composition or formulation is administered nutritional composition is liquid or semi-liquid and is administered in a dosage of about 100 to about 300 ml, such as, of about 150 to about 250 ml, such as, about 200 ml.

39. Use according to any of clauses 33-38, wherein the composition or formulation is administered in at least one time per day, such as, at least two times, at least three times, at least four times, at least 5 times or at least six times per day.

40. Method for treatment, prevention and/or reduction of malnutrition, weight loss and/or muscle atrophy in a mammalian subject, comprising administering a liquid or semi-liquid nutritional composition according to any one of clauses 1-12, a powder formulation according to any one of clauses 13-17 or a nutritional composition according to any one of claims 18-26, to said subject.

41. Method according to clause 40, wherein the mammalian subject is a human.

42. Method according to any of clauses 40 and 41, wherein the composition or formulation is administered in a dosage of about $\frac{1}{7}$ to about $\frac{1}{5}$ of the daily energy intake of the subject.

43. Method according to clause 42, wherein the composition or formulation is administered in a dosage of about $\frac{1}{6}$ of the daily energy intake of the subject.

44. Method according to any of clauses 40-43, wherein the composition or formulation is administered in a dosage comprising about 200 to about 500 Kcal, such as, of about 250 to about 350 Kcal, such as, about 300 Kcal.

45. Method according to any of clauses 40-44, wherein the composition or formulation is administered nutritional composition is liquid or semi-liquid and is administered in a dosage of about 100 to about 300 ml, such as, of about 150 to about 250 ml, such as, about 200 ml.

46. Method according to any of clauses 40-45, wherein the composition or formulation is administered in at least one time per day, such as, at least two times, at least three times, at least four times, at least 5 times or at least six times per day.

EXAMPLES

Example 1. Body Mass and Muscle Weight after Malnutrition and Subsequent Intake of Different Nutritional Compositions The aim of this study was to establish conditions for nutritional weight gain products in order to assess the effects of a novel nutritional composition with respect to weight gain and body composition, in the context of metabolic organ health and low-grade inflammation. The design of the study is shown in FIG. 1. Fifty matured male C57BL/6 mice, with a start weight of 25-28 g, were housed individually. A standard chow rodent diet (R/M Sniff® standard) was used as the basic food and sufficient water was provided ad libitum throughout the entire experiment.

Prior to the start of the experiment, all mice were acclimatized for two weeks during which their food intake of standard rodent diet (100% chow) was determined individually per mouse. Group 1 (n=5) was sacrificed on study day 1 to establish reference values for hind limb gastrocnemius, quadriceps and soleus muscle mass at the beginning of the study (baseline). Group 2 (n=5) was kept on normal, 100% chow conditions throughout the entire experiment until sacrifice at the end of study time point, to calculate and compare body and muscle weights with those of the intervention Groups 3-6. On day 0 the caloric restriction phase started, also referred to as the 'starvation' phase: Animals in Groups 3-6 (in total 40 animals) received 60% of their typically consumed chow diet under ad lib conditions (which was set as 100 kcal % as determined individually in the preceding acclimatization period). This feeding regime was maintained until an average weight loss of ~23% was reached over all Groups. Group 3 (n=10) was sacrificed at t=14 d to define the effect of the caloric restriction: decrease in total body weight and the rate of muscle wasting. For the subsequent weight gain phase (also referred to as 'refeeding' phase), the remaining 30 animals were matched on body weight and evenly divided over Groups 4, 5, and 6 (10 animals per group). From t=14 onwards, these caloric-restricted animals continued on their 60 kcal % chow diet supplemented with the predefined amounts of the weight gain products, according to the following schedule:

Group 4 (n=10): 60 kcal % chow+40 kcal % chow, equaling a 100% baseline food intake using chow standard diet;

Group 5 (n=10): 60 kcal % chow+Nutridrink Compact Protein (Nutridrink CP) in an amount equaling 40 kcal % from baseline energy intake;

Group 6 (n=10): 60 kcal % chow+Vital01 in an amount equaling the protein content (in grams) of Nutridrink CP as provided to Group 5.

The caloric restriction and refeeding regimen was based on Gallardo et al. (Gallardo C M. et al. 2014. Behavioral and neural correlates of acute and scheduled hunger in C57BL/6 mice. *Plos One* 9(5):1-12) and Williams et al. (Williams T D. et al. 2002. Cardiovascular responses to caloric restriction and thermoneutrality in C57BL/6J mice. *Am J Physiol Regulatory Integrative Comp Physiol* 282:R1459-R1467) who showed a rapid decline in body weight and subsequent stabilization within 14 to 21 days. Nutridrink CP is a nutritionally complete, and commercially available medical food sold by Nutricia, the Netherlands. Nutricia is a company wholly owned by Danone. Essentially the same product is also sold under the name Fortisip Compact Protein. The version that was used in this example contains 240 kcal per 100 ml with the characteristics as shown in Table I.

TABLE I

Content of the energy delivering compounds in Nutridrink Compact Protein (taken from the accompanying leaflet). Minerals, trace elements, vitamins, salts and fluids are not listed here.

| | |
|---|---|
| Fat (35 energy %) | 9.4 g |
| Saturated | 0.9 g |
| Monounsaturated fat | 5.7 g |
| Polyunsaturated fat | 2.8 g |
| linoleic acid | 2.1 g |
| α-linolenic acid | 0.4 g |
| Carbohydrates (41 energy %) | 24.4 g |
| Glucose | 0.2 g |
| Lactose | 0.3 g |
| Maltose | 0.8 g |
| Sucrose | 12.0 g |
| Polysaccharides | 11.0 g |
| Other | 0.1 g |
| Protein (24 energy %) | 14.4 g |
| Casein | 13.4 g |
| Whey | 1.0 g |

The macronutrient composition as well as the caloric value of the test compounds according to the present invention (Vital01) differ from Nutridrink CP that contains 14.4 g/100 ml total dairy protein comprising a casein:whey ratio of approximately 93:7. As noted above, for each Group 5, and 6, equal amounts of protein (in grams) were administered. Nutridrink CP was handled as recommended by the manufacturer. Vital01 was prepared by adding 35 mg ursolic acid to 100 ml Vital00, the content of which is provided in Table II.

TABLE II

Ingredients of Vital00, which is the basis for Vital01, a nutritional composition of the present invention. The listed amounts indicate percentages weight/volume that when dispersed up to a total volume of 100 ml in water represents a typical ⅙ daily portion for the treatment of malnutrition.

| Ingredient | % (w/v) |
|---|---|
| Total protein | 10% |
| Casein protein (6%) | |
| Whey protein (4%) | |
| Carbohydrates (maltodextrin and sugars) | 21.30% |
| Fats/oil | 7.50% |
| Essential amino acids | |
| valine (total of free and bound) | 0.80% |
| isoleucine (total of free and bound) | 0.80% |
| leucine (total of free and bound) | 2.00% |
| Salt and minerals | 0.64% |
| (potassium phosphate, sodium citrate, potassium chloride, potassium hydroxyde, sodium chloride, magnesium citrate, magnesium chloride, ferric pyrophosphate, calcium chloride, zinc sulfate, sodium selenite, manganese sulfate, copper sulfate, sodium fluoride, chromium chloride, sodium molybdate, potassium iodide) | |
| Vitamins | 0.07% |
| (vitamin C, vitamin E, vitamin A, vitamin B3, vitamin D, pantothenic acid, vitamin K1, vitamin B1, vitamin B6, vitamin B2, folic acid anhydrous, biotin, vitamin B12). | |
| Emulsifier and flavor | 0.20% |

During the weight gain phase, the animals were monitored daily by Echo-MRI (which was performed according to the manufacturer's instructions, EchoMRI LLC, Houston, USA). Body weight and food intake as well as intake of the weight gain products were determined daily. Upon sacrifice, muscles (gastrocnemius, quadriceps, tibialis and soleus) of both hind limbs were collected and muscle weights were determined. Following weighing of muscles from both the right and left hind limbs, one gastrocnemius, one quadriceps, one tibialis and one soleus muscle was fixed in formaldehyde and embedded in paraffin (for histology purposes). The gastrocnemius, quadriceps, tibialis and soleus muscle from the other hind leg was snap-frozen and stored at −80° C. for future RNA analysis. Also the liver was isolated, weighed and stored at −80° C. Plasma was collected by heart puncture. All procedures were standard, in accordance with protocols and guidelines that were prior approved by the Animal Ethics Committee, and performed using general methodology known to the person skilled in the art.

In short, the experiment was performed as follows: in the starvation period, adult male mice were maintained on 60% of a regular chow diet (based on the 100% intake in the two weeks prior to day t=0), until their average bodyweight dropped about 25%. In the following refeeding phase, mice were stratified in three groups of 10, and the 60% chow diets were supplemented with either standard chow, Nutridrink CP, or with Vital01 according to the following calculation: For the control group, mice were fed with standard chow to 100% of a regular mouse diet (which is approximately 5 g/day). Hence, 40% (generally about 2 g) additional chow was provided to the mice in control Group 3. The number of calories in 2 g chow was used to calculate an iso-caloric amount of Nutridrink CP, containing 0.47 g protein and this same amount of protein was provided to animals in the last group by means of Vital01 supplementation. Table III summarizes the amounts and nutritional values of the various groups. Given the different formulations of Nutridrink CP and Vital01, it is clear that when the amount of protein is normalized, the value of the energy in kcal differs between the food taken by the group receiving Nutridrink CP and the groups receiving Vital01. The choice for normalizing the protein content was based on the fact that the primary objective of this experiment was to compare the effects of ursolic acid and the different casein/whey ratios of Nutridrink CP and Vital01 on weight gain, and in particular gain of muscle mass which is mainly a result of protein uptake and synthesis and not fat accumulation or energy intake.

TABLE III

Comparison of nutritional characteristics of diets provided to the experimental groups

| | Values per | | | |
|---|---|---|---|---|
| | 60% chow | 100% chow | 60% chow + Nutridrink CP | 60% chow + Vital01 |
| Energy (kcal) | 11.664 | 19.44 | 19.44 | 21.46 |
| Fat (g) | 0.099 | 0.165 | 0.40 | 0.45 |
| Carbohydrates (g) | 1.635 | 2.725 | 2.43 | 2.64 |
| Protein (g) | 0.57 | 0.95 | 1.04 | 1.04 |

Results

Figure 3:
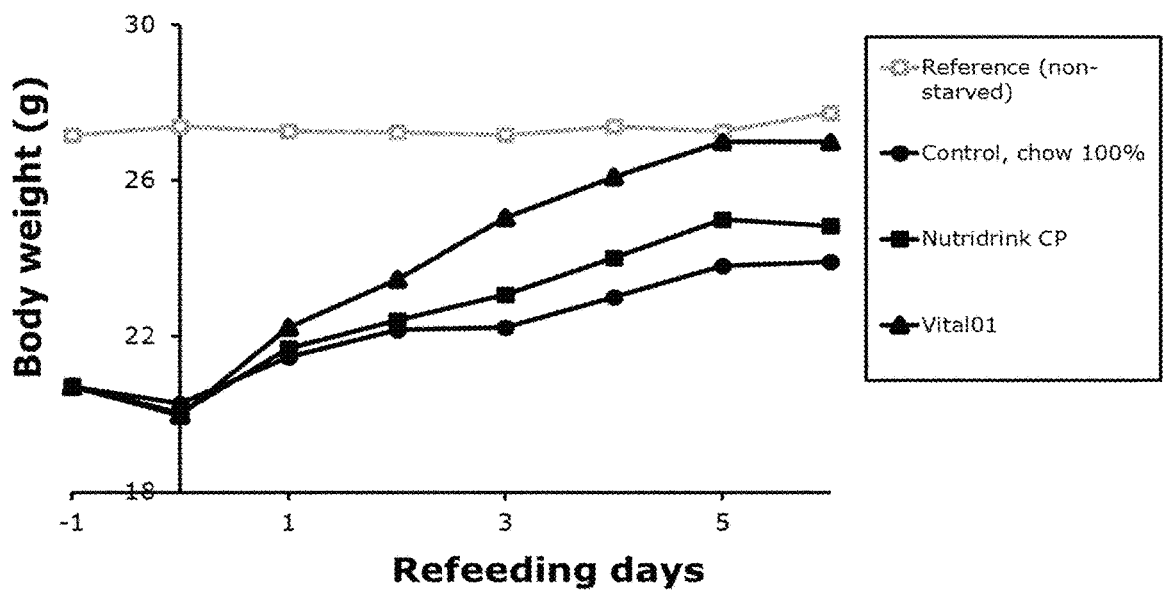
FIG. 3 shows the effect on total body weight (in grams) after refeeding with normal amounts of standard mouse feed (Ssniff R/M diet, 100% chow control), and the novel composition of the present invention, referred to as Vital01. For sake of comparison, the commercially available and widely prescribed Nutridrink CP formulation was provided to one group of animals. Surprisingly, and exceeding the initial expectations of the investigators, the animals receiving Vital01 gained body weight much faster than was anticipated. While half of the animals in the Vital01 group reached normal, full body weight already after 5 days of refeeding (on average 96% of the weight loss was regained), animals in the control group on chow had regained only 47% of the weight loss, while animals on Nutridrink CP had regained just 65% of weight loss within 5 days of refeeding on average. To maximize the window of analysis, it was therefore decided to start sacrificing the animals after 6 days of refeeding (corresponding to t=20 in the original study design as depicted in FIG. 1).
Figure 4:
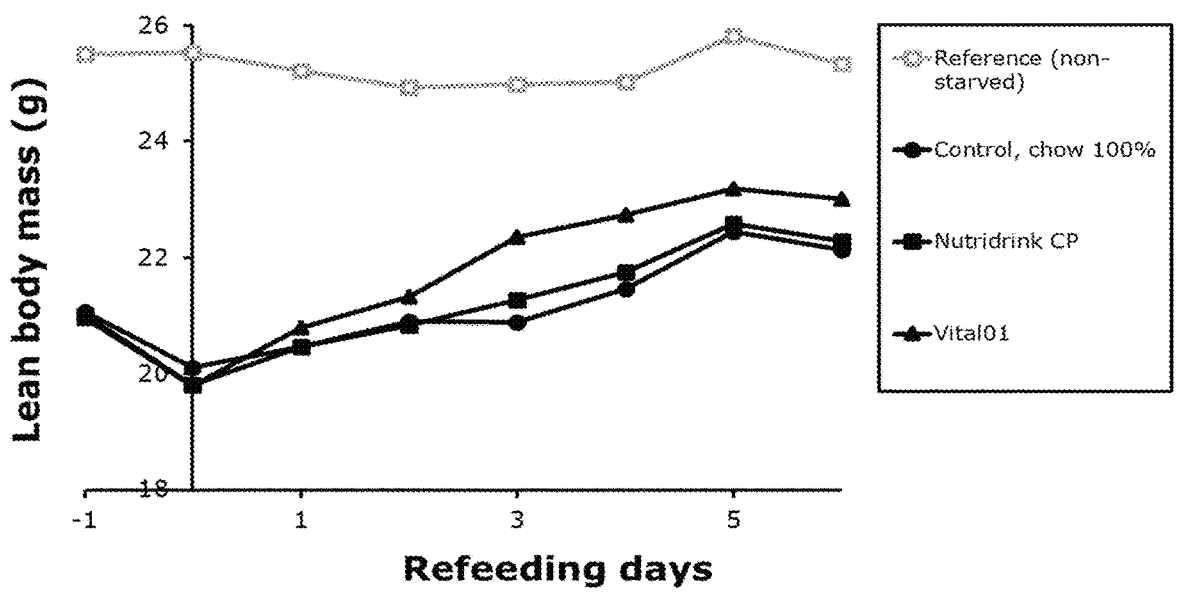
FIG. 4 shows the effects on Lean body mass (in grams) after refeeding with normal 100% chow (control), and the compositions Nutridrink CP and Vital01. Again, the Vital01 composition refeeding resulted in a faster gain of lean body mass in comparison to the Nutridrink CP and 100% chow control.

The effect of food restriction over time is shown in FIG. 2. The mice in Groups 3-6 were held on a 60 kcal % diet as compared to the two weeks preceding the food restriction period and lost in average 5-6 grams in total body weight (~23%). Upon refeeding according to the schedules discussed above, the mice started to gain weight almost instantly, see FIG. 3. The control Group 4 that received their normal 100 kcal % diet as before the starvation period gained weight relatively slowly. Unexpectedly, animals in the group receiving Vital01 (Group 6), displayed a very rapid increase in total body weight that was significantly higher than the group that received Nutridrink CP (Group 5). That the increase in total body weight was not solely due to increase in (for example) fat buildup (since slightly more kcal were provided in the Vital groups) can be seen in FIG. 4 that shows the increase in lean body mass, wherein also the Vital01 group showed a faster increase than the Nutridrink CP and control Group (that displayed a comparable increase in lean body mass). It is concluded that the Vital01 composition caused a significant faster increase in total body weight as well as in lean body mass in mammalian subjects that suffered from a decreased body weight after two weeks of starvation on a 60 kcal % diet. Due to the surprisingly fast increase in bodyweight as observed for the Vital01 group, the study was ended sooner than anticipated by sacrificing the animals already on day 6 of the refeeding phase.

Figure 5:
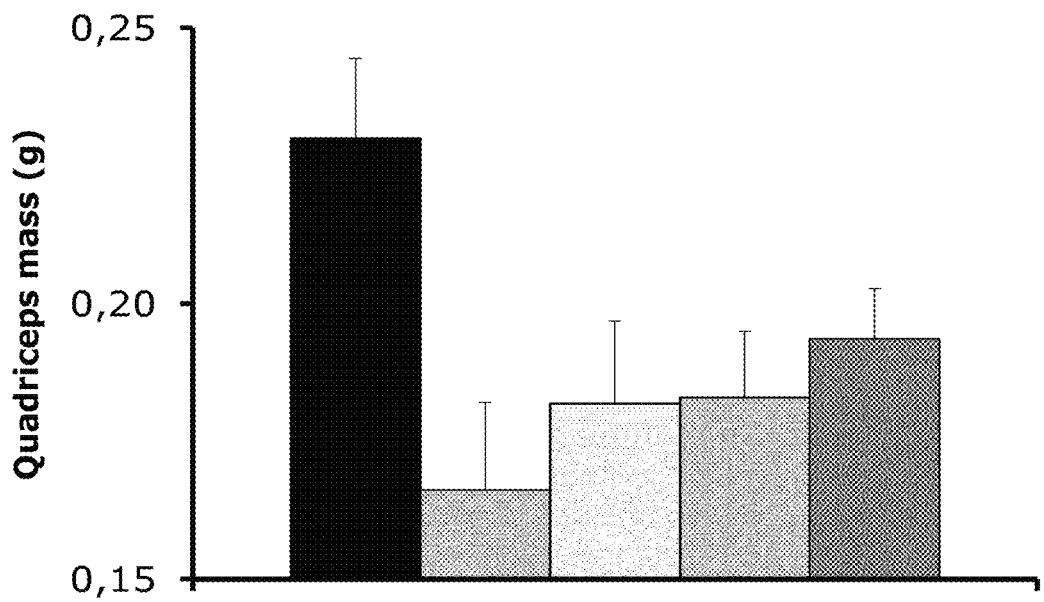
FIG. 5 is a bar diagram showing the mass (in grams) of the quadriceps muscle after refeeding and sacrifice. The bars represent (from left to right): the chow baseline, the muscle wasting group, the control 100% chow refed group, the Nutridrink CP group and the Vital01 group. The increase in mass observed in all refeeding groups was significant in relation to the muscle wasting group whereas only for the Vital01 group, the increase in quadriceps mass observed was significant in comparison to the chow 100% control group.
Figure 6:
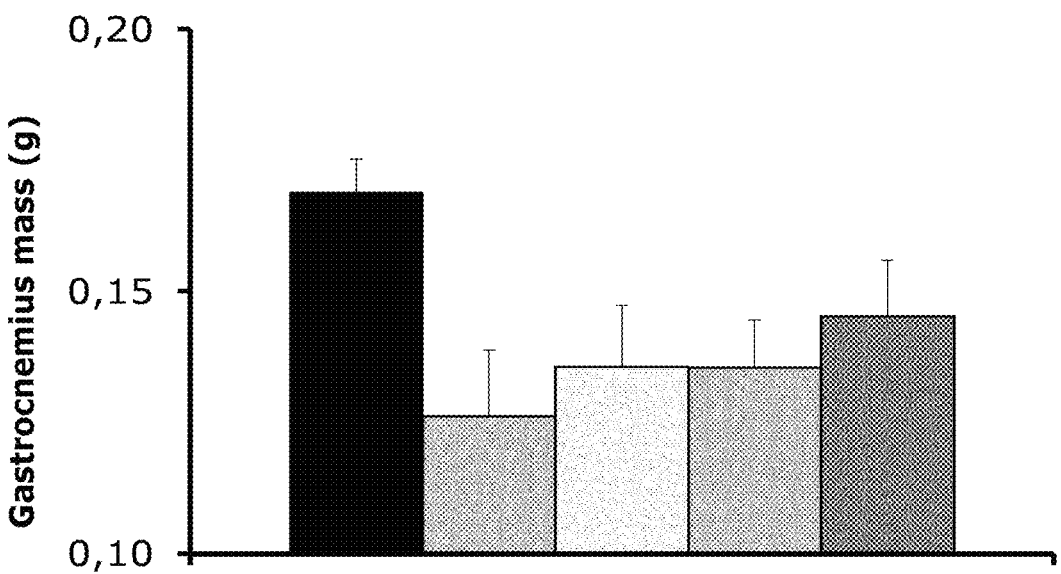
FIG. 6 is a bar diagram showing the mass (in grams) of the gastrocnemius muscle after sacrifice and after refeeding. The bars represent (from left to right): the chow baseline, the muscle wasting group, the control 100% chow refed group, the Nutridrink CP group and the Vital01 group. The increase in mass observed in all refeeding groups was significant in relation to the muscle wasting group whereas the increase in gastrocnemius mass observed in the Vital01 group was significant in comparison to the chow 100% control group and to the Nutridrink CP group.
Figure 7:
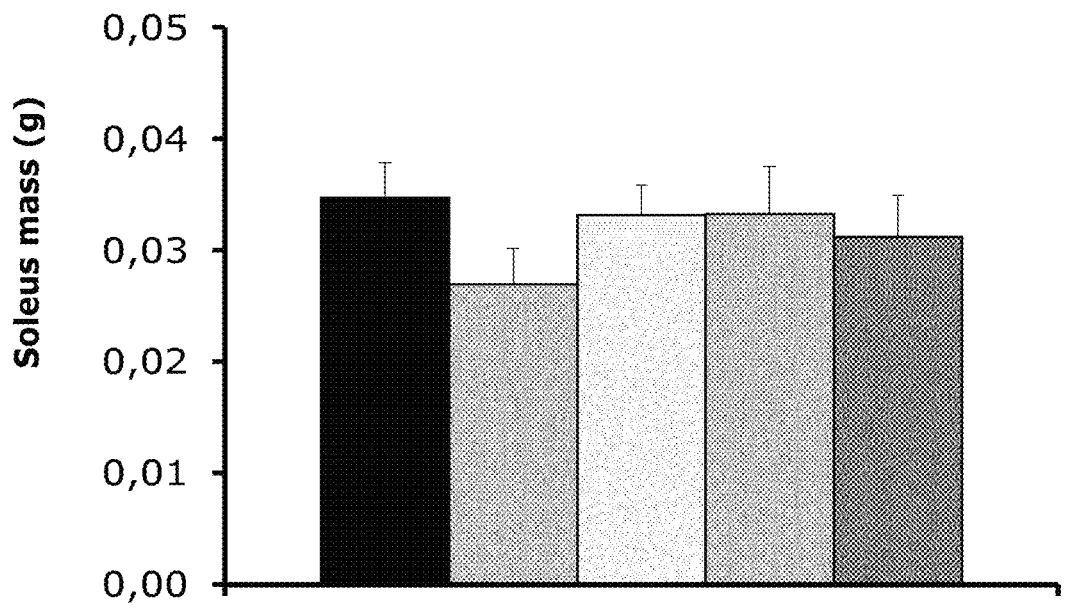
FIG. 7 is a bar diagram showing the mass (in grams) of the soleus muscle after sacrifice and after refeeding. The bars represent (from left to right): the chow baseline, the muscle wasting group, the control 100% chow refed group, the Nutridrink CP group and the Vital01 group. No significant difference in mass of this particular muscle was observed between the different refeeding groups. The mass of the muscle returned to normal levels after refeeding in all refeeding groups.
Figure 8:
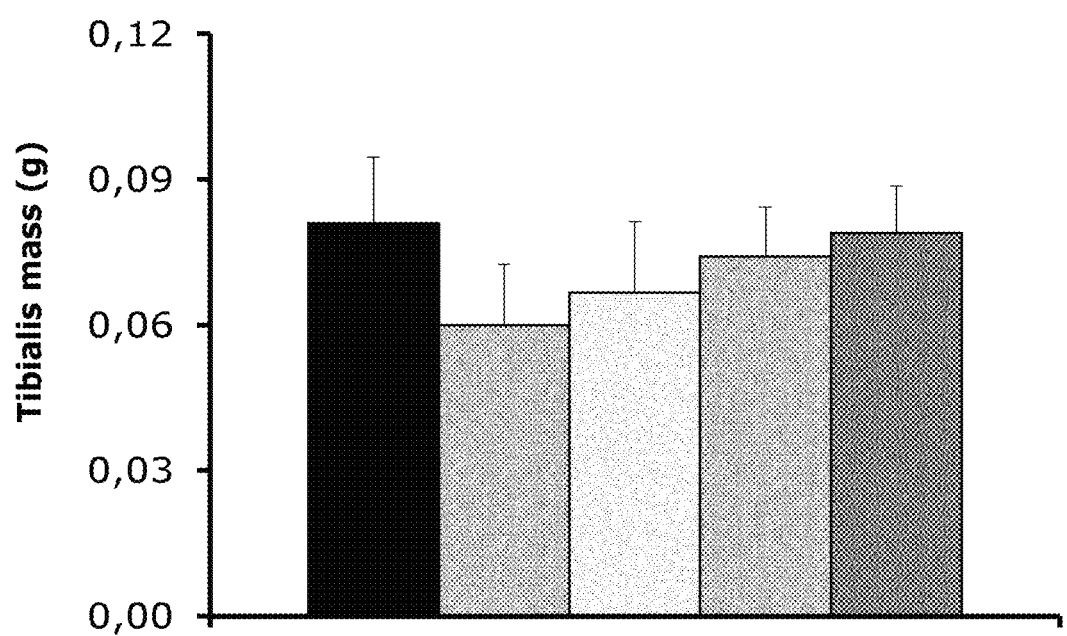
FIG. 8 is a bar diagram showing the mass (in grams) of the tibialis muscle after sacrifice and after refeeding. The bars represent (from left to right): the chow baseline, the muscle wasting group, the control 100% chow refed group, the Nutridrink CP group and the Vital01 group. Although the increase in mass in the Nutridrink CP and Vital01 groups versus the 100% chow control group was measured, no significant difference in mass of this particular muscle was observed between the different refeeding groups.
Figures 9, 10:
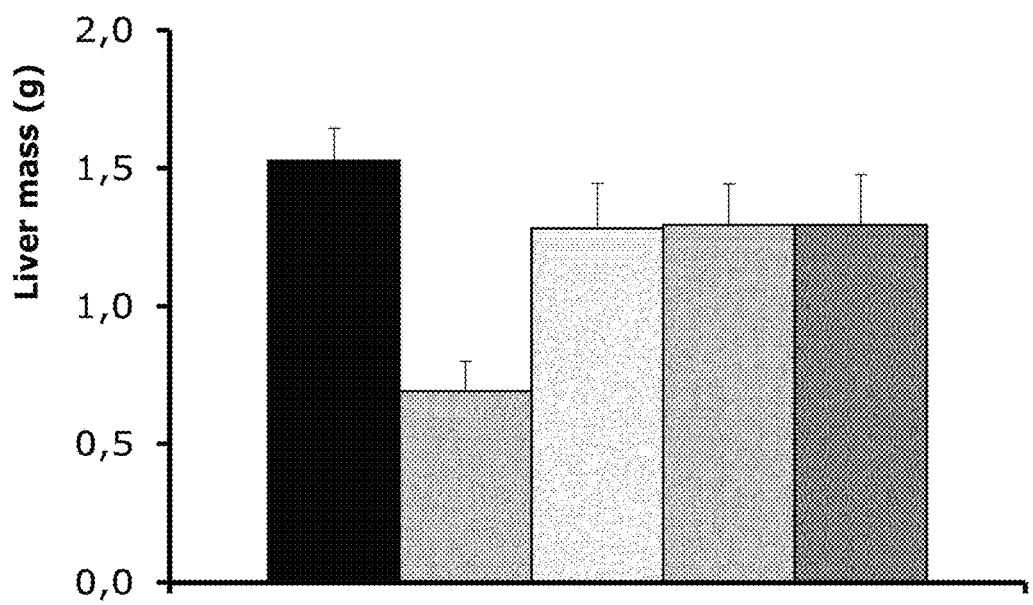
FIG. 9 is a bar diagram showing the mass (in grams) of the liver after sacrifice and after refeeding. The bars represent (from left to right): the chow baseline, the muscle wasting group, the control 100% chow refed group, the Nutridrink CP group and the Vital01 group. The liver had lost a significant mass upon starvation and regained mass upon refeeding in all refeeding groups, reaching almost normal levels just before sacrifice. No difference in increase in liver mass was observed between the different refeeding groups.
FIG. 10 shows the statistic calculations for differences between groups in bodyweight and in muscle weight in SPSS using a non-parametric Kruskall-Wallis test followed by Mann-Whitney. P-values for comparison of bodyweight (n=10) between groups on day 0 (start refeeding protocol) up to day 6 (sacrifice) are provided. It is noted that a small P value ($<0.05$) means that the differences in bodyweight that were measured are unlikely to be due to random sampling.

To further elucidate the effects of the Vital01 composition on specific muscles, the weight of 4 different muscles was determined at the end of the experiment and compared to the respective control groups. FIG. 5 shows the weight of the quadriceps muscle at sacrifice. Although in the relatively short period of refeeding, the weight of the quadriceps did not reach baseline values as were determined in the reference group (Group 1), all groups that received refeeding did clearly build up the quadriceps muscle in comparison to non-refed animals in Group 3. Also, it shows that the Vital01 group reached a quadriceps mass that was higher than the control Group 4 (100 kcal % chow) and Group 5 (Nutridrink CP). FIG. 6 shows the increase in the gastrocnemius mass. Again, refeeding with the Vital01 composition resulted in a greater increase in mass of this particular muscle. Importantly the groups of mice were relatively small, but the increase obtained with Vital01 (Group 6, right bar) appeared statistically significant over the increase observed with Nutridrink CP (4th bar), which shows that the protein composition of the Vital01 formulation might be more beneficial in the treatment of muscle wasting that the protein composition present in Nutridrink CP. Moreover, it suggests strongly that the ursolic acid that is added to the Vital01 composition beneficially attributes to the muscle mass increase, especially when the mass of the gastrocnemius is observed. FIG. 7 shows that no significant difference was observed in soleus muscle mass between all refeeding groups. Importantly, this muscle did not suffer as much from wasting as the quadriceps and gastrocnemius muscles (FIGS. 5 and 6 respectively). Whereas the decrease in soleus mass was significant upon starvation, all refeeding schedules resulted in a more or less normal mass. FIG. 8 shows the mass of the tibialis, and similar to the soleus muscle, the tibialis shows a relatively modest atrophy upon starvation when compared to the quadriceps and gastrocnemius muscles. Still, it appears that refeeding with the Vital01 composition resulted in a more or less normal tibialis mass, while both the control group with 100 kcal % chow (Group 4) and Nutridrink CP (Group 5) were trailing behind. Because it could not be excluded that the increase in total body weight was attributable to an increase in liver size, the mass of the liver was also addressed for all experimental groups. FIG. 9 shows that no difference was observed between the different refed groups, although there was a clear decrease in liver mass upon starvation (Group 3 (second bar) compared to Group 1 (first bar)) that was reversed in all refeeding groups.

Nutridrink CP and Vital01 were both provided as liquid formulations which, due to low volumes and spillage, could not be administered to the mice in their regular drinking bottles. To this end, and to accurately monitor and control intake of test products, both Nutridrink CP and Vital01 were 'gellified' by the addition of the non-metabolizable hydroxypropyl methylcellulose to form a semi-solid gel that could readily be fed to the animals in a petridish. The daily volume of gellified Nutridrink CP and Vital01 that mice received was 3.3 ml Nutridrink CP or 4.9 ml Vital01. 100% chow corresponds to approximately 5 g dry weight, and mice in all groups were provided with water ad lib. Statistics for differences between groups in total body weight and in muscle weight were calculated in SPSS using a non-parametric Kruskall-Wallis test followed by Mann-Whitney. P-values for comparison of bodyweight (n=10) between groups on day 0 (start of the refeeding protocol) up to day 6 (sacrifice) are given in FIG. 10. It is stressed here that a small p value (<0.05) means that the differences in body-weight that were measured are likely not due to random sampling. The same statistic methods were employed for muscle mass measurements in all groups. It should be noted that the increase in muscle mass in mice treated with Vital01 is significant over the values found with Nutridrink CP (indicated in FIG. 11 by an asterisk).

In conclusion, it is held that when mammalian subjects (in this experiment normal male mice) suffer from muscle wasting upon malnutrition, even to a level wherein the total body weight is decreased to about 75% of their normal weight, that such can be reversed by refeeding with a normal diet and with medical nutrition formulations known in the art, but that the nutritional composition of the present invention was able to let the subjects regain weight much faster than the formulations of the known art. Total body weight and muscles like the tibialis were on their normal weight again already within one week of refeeding with the compositions of the present invention whereas this was not the case when normal animal feed or compositions of the prior art were administered. Moreover, there appears to be a beneficial effect of ursolic acid in the compositions of the present invention in at least some muscles (such as the quadriceps and the gastrocnemius).

Example 2. Determination of Ursolic Acid in Plasma after Refeeding

It is known in the art that ursolic acid has an extremely low bioavailability. For instance, a study investigating the intestinal uptake of ursolic acid (from an ethanolic extract of *Sambucus chinensis*) found that a dose of 80 mg/kg bodyweight ursolic acid had an oral bioavailability of only 0.6% (Liao Q, et al. 2005, LC-MS determination and pharmacokinetic studies of ursolic acid in rat plasma after administration of the traditional chinese medicinal preparation Lu-Ying extract. *Yakugaku Zasshi* 125(6):509-515). Others have been unable to detect ursolic acid in blood or tissues upon oral administration, despite observing clear physiological or pharmacological responses to ursolic acid. This may have been due to the low bioavailability and/or by the lack of sensitive methods to measure ursolic acid levels in situ.

To confirm that ursolic acid was actually taken up in the context of Vital01, a highly sensitive analytical method was developed to measure ursolic acid in the small volumes of plasma that were obtained from sacrificed animals in the weight gain experiment. For this, a highly sensitive UPLC-MS was used, essentially as described by Xia et al. (Quantitation of ursolic acid in human plasma by ultra-performance liquid chromatography tandem mass spectrometry and its pharmacokinetic study. *J Chromatography* 2011 879(2):219-224), albeit with significant modifications to enable analysis of small volume samples of mouse or human plasma. Since conversion of ursolic acid into its isomer oleanolic acid has been described to occur in animal studies, the method was further modified to simultaneously measure both ursolic acid and oleanolic acid.

Results

The following modifications to the published UPLC-MS method by Xia et al. (2011) were implemented and validated to enable simultaneous analysis of ursolic acid and oleanolic acid in small volumes of plasma, while ensuring high specificity and sensitivity of the method:

To increase dissolution of ursolic acid, acetonitrile was supplemented with 50% methanol to the mobile phase and stock solutions were prepared in methanol instead of acetonitrile;

Because initial injections showed carry over, a drop of ammonia was added;

To improve resolution between ursolic and oleanolic acid, the C8 column as described by Xia et al. (2011) was replaced by a 018 column (Waters Acquity BEH C18 50×2.1 mm, 1.7 μm);

Volumes for sample preparation were reduced using ethylacetate for extraction and evaporation;

Column temperature was optimized and changed from 30 to 40° C.;

Reconstitution volume was changed from 200 μL to 100 μL.

Using the optimized settings for chromatography, MS detection and sample preparation, a method was developed that enabled simultaneous measurements of ursolic acid and oleanolic acid in less than 30 μL of plasma with a quantitation range of 5-5000 ng/ml. The optimized method was then used to analyze 20 μL of EDTA plasma samples from animals in Groups 4, 5, and 6 that were collected during sacrifice after 6 days of refeeding and stored at −80° C. until analysis. No ursolic acid (detection <LOD, which was 4.94 ng/ml) could be detected in plasma samples derived from animals refed with 100% chow (Group 4), or from animals refed with Nutridrink CP (Group 5). However, ursolic acid was readily detectable in plasma samples taken from animals refed with Vital01 (Group 6), with an average concentration of 76.6±8.8 ng/ml. Given that the animals (in all groups) had finished all of their food in the morning, and that they were sacrificed in the afternoon without intermittent feeding, suggests that formulation of ursolic acid in Vital01 significantly increases its bioavailability. This may have been facilitated by increased solubilization of ursolic acid through fats and lipids which are present in the composition of the present invention and/or possibly by complexing to proteins or amino acids in Vital01 to facilitate and enhance its transport over the gut wall.

Example 3. Clinical Trial on Elderly Human Subjects

Rationale: The prevalence of malnutrition in The Netherlands is well over 20% among people aged 75 or older. Malnourishment significantly and negatively impacts clinical parameters such as weight loss, wound healing, reduced physical performance, lethargy and depression, impaired immune function, and secondary complications. One of the major direct effects of disease-related malnutrition is muscle loss which impairs function, mobility and independence. Malnutrition can be detected by low body weight and by involuntary weight loss, but also by atrophy of muscle tissue leading to reduced strength and thus impaired mobility. In older adults the age-related progressive loss of skeletal muscle mass and strength (sarcopenia), leads to the loss of functional capacity and an increased risk of developing chronic metabolic disease. Improving the nutritional status of patients will lead to a better physical condition which is very relevant for a quicker recovery from the underlying disease.

Objective: A study is performed to investigate the impact of the oral nutritional supplementation (Vital02) composition of the present invention, primary on body weight and lean body mass and secondary on physical performance, muscle health and immune function in malnourished elderly people versus a nutritional supplement (ONS) which is the standard of care in The Netherlands for the treatment of malnutrition.

Study design: Over a period of 12 weeks, a randomized and controlled intervention trial is executed with 2 treatments in parallel: Treatment 1: Vital02 (n=40), 2 portions of Vital02 (600 kcal); Treatment 2 (reference): ONS (n=40), 2 portions of a standard Food for Medical Purposes (600 kcal).

Study population: Elderly subjects (≥65 y) with malnutrition or risk for malnourishment as assessed by the MNA (mini nutritional assessment).

Main study parameters/endpoints: The main interest is in the mean differences in change in body weight (kg) and lean body mass (kg) between treatment 1 vs. treatment 2. Furthermore, physical performance, muscle health and immune function are assessed.

Vital02 comprises 465.02 Kcal per 100 g of powder composition. Table IV gives the composition of the Vital02 powder, which is used for the preparation of a liquid composition administered to the subjects. Table V gives the total amino acid content of Vital02, from which the percentage of Isoleucine, Valine and Leucine of the total amino acid content can be derived.

TABLE IV

Ingredients of Vital02 powder.

|  | w/w % |
|---|---|
| Fat | 18.43 |
| Carbohydrate | 51.48 |
| Fiber | 0.04 |
| Protein | 22.92 |
| Salt | 0.39 |
| Ursolic acid | 0.1634612 |
| Minerals | |
| Calcium | 0.1931613 |
| Chromium | 0.0000222 |
| Chlorine | 0.1815838 |
| Phosphor | 0.1016971 |
| Iron | 0.0051262 |
| Iodine | 0.0000396 |
| Potassium | 0.2970668 |
| Copper | 0.000542 |
| Magnesium | 0.0520789 |
| Manganese | 0.0009577 |
| Molybdenum | 0.000025 |
| Sodium | 0.156773 |
| Selenium | 0.000025 |
| Zinc | 0.0034443 |
| Vitamins | |
| Vitamin B1 (thiamine) | 0.0004969 |
| Vitamin B2 (riboflavin) | 0.000651 |
| Vitamin B3 (niacin) | 0.0068566 |
| Vitamin B5 (pantothenate) | 0.0015751 |
| Vitamin B6 (pyridoxine) | 0.0005338 |
| Vitamin B9/B11 (folic acid) | 0.0001322 |
| Vitamin B12 (cobalamin) | 8.987E−07 |
| Vitamin C (ascorbic acid) | 0.0315036 |
| Vitamin D3 (cholecalciferol) | 0.0000086 |
| Vitamin E (tocopherol) | 0.0013929 |
| Vitamine B7 (biotin) | 0.0000092 |
| Vitamin K1 (phylloquinone) | 0.0000157 |
| Vitamin A (retinol) | 0.0000291 |
| Choline | 0.1111477 |
| Essential amino acids | |
| L-valine | 1.050346 |
| L-leucine | 1.087395 |
| L-isoleucine | 3.2 |

TABLE V

Total amino acid content of Vital02

| Amino acids | w/w % |
|---|---|
| L-valine | 2.0717 |
| L-leucine | 4.8057 |
| L-isoleucine | 2.0312 |
| L-alanine | 0.635 |
| L-arginine | 0.449 |
| L-aspartic acid | 1.4342 |
| L-cysteine | 0.2086 |
| L-glutamic acid | 3.0979 |
| Glycine | 0.2491 |
| L-lysine | 1.3985 |
| L-histidine | 0.3717 |
| L-methionine | 0.3953 |
| L-phenylalanine | 0.6393 |
| L-proline | 1.2106 |
| L-serine | 0.8338 |
| L-threonine | 0.883 |
| L-tryptophane | 0.2135 |
| L-tyrosine | 0.6329 |

The invention claimed is:

1. A method for treating a human patient suffering from malnutrition, comprising administering a liquid or semi-liquid nutritional composition comprising:
   90 to 130 mg/ml dairy proteins;
   32 to 55 ng/ml vitamin D or a derivative thereof; and
   0.3 to 0.9 mg/ml ursolic acid;
   wherein the casein:whey ratio in said dairy proteins ranges from 45:55 to 65:35 and wherein 30 to 45% of the total amino acid content is a mixture of leucine, isoleucine and valine comprising valine and isoleucine both in a concentration of 7 to 10% of the total amino acid content and leucine in a concentration of 16 to 25% of the total amino acid content, and wherein valine, isoleucine and leucine are present in free and bound form.

2. The method according to claim 1, comprising from about 1.5 to about 3 Kcal/ml.

3. The method according to claim 1, wherein the liquid or semi-liquid nutritional composition is made by combining a powder formulation comprising suitable amounts of dairy proteins; vitamin D or a derivative thereof; ursolic acid, and an amino acid premix comprising free leucine, free isoleucine and free valine with a suitable carrier.

4. The method according to claim 3, wherein the suitable carrier is water.

5. The method according to claim 3, wherein the liquid or semi-liquid nutritional composition is made by combining one gram of the powder formulation with from about 1.5 to about 3 ml of the suitable carrier.

6. The method according to claim 1, wherein the liquid or semi-liquid nutritional composition is made by combining a powder formulation comprising suitable amounts of an amino acid premix comprising free leucine, free isoleucine and free valine; vitamin D or a derivative thereof; and ursolic acid with a dairy-protein containing product such as milk or yoghurt.

7. The method according to claim 6, wherein the dairy-protein containing product is milk or yoghurt.

8. The method according to claim 1, wherein the patient is 65 years old or older.

9. A method for treating a human patient suffering from malnutrition, comprising administering a nutritional composition comprising per 100 Kcal:
   from about 4.0 to about 6.0 grams dairy proteins;
   from about 1.65 to about 2.2 μg vitamin D or a derivative thereof;
   and from about 25 to about 44 mg ursolic acid;
   wherein the casein:whey ratio in said dairy proteins is from 45:55 to 65:35 and wherein 30 to 45% of the total amino acid content is a mixture of leucine, isoleucine and valine comprising valine and isoleucine both in a concentration of 7 to 10% of the total amino acid content and leucine in a concentration of 16 to 25% of the total amino acid content, and wherein valine, isoleucine and leucine are present in free and bound form.

10. The method according to claim 9, wherein the patient is 65 years old or older.

* * * * *